US 7,752,060 B2

(12) United States Patent
Hicks et al.

(10) Patent No.: US 7,752,060 B2
(45) Date of Patent: Jul. 6, 2010

(54) INTERNET SYSTEM FOR CONNECTING HEALTHCARE PROVIDERS AND PATIENTS

(75) Inventors: David G Hicks, Littleton, CO (US);
Scott Montroy, Lakewood, CO (US);
John Neal, Tampa, FL (US)

(73) Assignee: Health Grades, Inc., Golden, CO (US)

( * ) Notice: Subject to any disclaimer, the term of this patent is extended or adjusted under 35 U.S.C. 154(b) by 909 days.

(21) Appl. No.: 11/512,529

(22) Filed: Aug. 29, 2006

(65) Prior Publication Data
US 2007/0185732 A1    Aug. 9, 2007

Related U.S. Application Data

(60) Provisional application No. 60/771,757, filed on Feb. 8, 2006.

(51) Int. Cl.
*A61B 5/00* (2006.01)
*G06F 19/00* (2006.01)
(52) U.S. Cl. .......................................................... 705/3
(58) Field of Classification Search ...................... 705/2, 705/3
See application file for complete search history.

(56) References Cited

U.S. PATENT DOCUMENTS

| | | | |
|---|---|---|---|
| 5,365,425 A | 11/1994 | Torma et al. .............. | 364/401 |
| 5,517,405 A | 5/1996 | McAndrew et al. | |
| 5,915,240 A | 6/1999 | Karpf | |
| 6,014,629 A * | 1/2000 | DeBruin-Ashton ............ | 705/2 |
| 6,029,138 A | 2/2000 | Khorasani et al. | |
| 6,081,786 A | 6/2000 | Barry et al. | |
| 6,088,677 A | 7/2000 | Spurgeon | |
| 6,108,635 A | 8/2000 | Herren et al. | |
| 6,188,988 B1 | 2/2001 | Barry et al. | |
| 6,269,339 B1 | 7/2001 | Silver | |
| 6,584,445 B2 | 6/2003 | Papageorge | |
| 6,658,431 B1 | 12/2003 | Norman, Jr. | |
| 6,671,714 B1 | 12/2003 | Weyer et al. | |

(Continued)

OTHER PUBLICATIONS

GeoAccess.com [online], [retrieved on Feb. 15, 2010]. Retrieved from the internet: <URL: http://www.ingenix.com> (2010) 1 page.

(Continued)

*Primary Examiner*—Gerald J. O'Connor
*Assistant Examiner*—Trang Nguyen
(74) *Attorney, Agent, or Firm*—Merchant & Gould, P.C.

(57) ABSTRACT

An Internet-based system involves a database and search capabilities for connecting patients with healthcare providers, e.g., physicians, hospitals, nursing homes, treatment facilities, etc., and further enables such providers to reach patients with whom they may not otherwise come into contact. A patient may access the healthcare provider information through a search conducted using a search engine, such as Google, Yahoo, etc. Alternatively, a patient may access the company Web site's predetermined Web page that provides search capabilities on its database. A patient may research a healthcare provider based on criteria specified by the patient. Information provided to the patient may be in the form of a report, profile, ratings, etc., including patient-provided information, physician-verified information, and information verified by an independent third party. The verified information and ratings provided by the Web site enable patients to differentiate among healthcare providers and thereby select the provider that best meets their individual needs.

17 Claims, 22 Drawing Sheets

U.S. PATENT DOCUMENTS

| | | | |
|---|---|---|---|
| 6,697,783 B1 | 2/2004 | Brinkman et al. | |
| 6,738,754 B1 | 5/2004 | Norman, Jr. | |
| 7,065,528 B2 | 6/2006 | Herz et al. | |
| 7,383,197 B1 | 6/2008 | Neuman | 705/2 |
| 2001/0039547 A1 | 11/2001 | Black et al. | |
| 2002/0038233 A1 | 3/2002 | Shubov et al. | 705/1 |
| 2002/0046041 A1 | 4/2002 | Lang | |
| 2002/0059201 A1 | 5/2002 | Work | |
| 2003/0028406 A1 | 2/2003 | Herz et al. | |
| 2003/0093294 A1* | 5/2003 | Passantino | 705/2 |
| 2003/0195838 A1* | 10/2003 | Henley | 705/37 |
| 2004/0010423 A1* | 1/2004 | Sameh | 705/2 |
| 2004/0019579 A1 | 1/2004 | Herz et al. | 707/104.1 |
| 2004/0064440 A1 | 4/2004 | Norman, Jr. | |
| 2004/0172282 A1 | 9/2004 | Benja-Athon | 705/2 |
| 2004/0193447 A1 | 9/2004 | Joseph | |
| 2004/0260666 A1 | 12/2004 | Pestotnik et al. | |
| 2005/0071189 A1 | 3/2005 | Blake et al. | |
| 2005/0149507 A1 | 7/2005 | Nye | |
| 2006/0015369 A1 | 1/2006 | Bachus et al. | 705/2 |
| 2006/0080146 A1* | 4/2006 | Cook et al. | 705/2 |
| 2006/0161456 A1* | 7/2006 | Baker et al. | 705/2 |
| 2006/0294138 A1 | 12/2006 | Stolba | 707/10 |
| 2007/0094044 A1 | 4/2007 | Stone et al. | 705/2 |

OTHER PUBLICATIONS

UCompareHealthCare.com [online], [retrieved on Feb. 15, 2010]. Retrieved from the internet: <URL: www.UCompareHealthCare.com> (2010) 1 page.

RevolutionHealth.com [online], [retrieved on Feb. 15, 2010]. Retrieved from the internet: <URL: www.RevolutionHealth.com> (No Date) 1 page.

WebMD.com [online], [retrieved on Feb. 15, 2010]. Retrieved from the internet: <URL: www.WebMD.com> (2005-2010) 2 pages.

GeoAccess.com (Ingenix.com) [online], [retrieved on Feb. 15, 2010]. Retrieved from the internet: <URL: http://www.ingenix.com> (Copyright © 2010) 1 page.

RevolutionHealth.com [online], [retrieved on Mar. 2, 2010]. Retrieved from the internet: <URL: www.RevolutionHealth.com> (Copyright © 2010) 3 pages.

UCompareHealthCare.com [online], [retrieved on Feb. 15, 2010]. Retrieved from the internet: <URL: www.UCompareHealthCare.com> (Copyright © 2010) 1 page.

Vitals.com [online], [retrieved on Mar. 2, 2010]. Retrieved from the internet: <URL: http://www.vitals.com/> (Copyright © 2006-2010) 2 pages.

WebMD.com [online], [retrieved on Feb. 15, 2010]. Retrieved from the internet: <URL: www.WebMD.com> (Copyright © 2005-2010) 2 pages.

* cited by examiner

Fig. 3B

353 — www.company.com Research Healthcare Providers www.company.com/Non-Member Profile

Non-Member Report — 354

Name / Specialty — 356
Location(s); Phone Number(s) — 358
Gender — 360
Professional Misconduct, if any — 362
Area Hospital Ratings — 364
Patient Experience Survey — 366
Comparisons to Averages — 368

INTERNET SYSTEM FOR CONNECTING HEALTHCARE PROVIDERS AND PATIENTS

RELATED APPLICATIONS

This application claims priority of U.S. provisional application Ser. No. 60/771,757, entitled "Internet System for Connecting Doctors and Patients," filed Feb. 8, 2006.

TECHNICAL FIELD

This invention generally relates to an Internet-based system and method that connects patients with potential healthcare providers, e.g., physicians and hospitals. More particularly, the present invention relates to providing on-line ratings and reports comprised of detailed healthcare provider information with verified information sections, including physician-verified and/or independent third-party-verified portions, and patient-provided information sections, to assist patients in differentiating among healthcare providers.

BACKGROUND

It is vital to potential patients to gain as much information as possible about a particular physician and/or treatment facility, e.g., a hospital, before selecting that particular physician as a primary care doctor or specialist or that particular place of treatment. The Internet has become a significant source of information to consumers in general. Indeed, consumers rely heavily on the Internet for information and data. However, one well-recognized problem with the Internet is that the patient often cannot assess the veracity of the information which is revealed through an Internet search query using a common search engine, such as Google, Yahoo, etc. Further, with regard to healthcare provider information in particular, there are few, if any resources available for patients to discover any information, much less verified information, about physicians or hospitals. Typically, any information about physicians or hospitals on the Internet is provided by the physicians or hospitals themselves (and, in some cases, insurance companies). Such information may not be updated on a regular basis or may contain inaccurate or incomplete information. Further, even if such information is available, it is usually not organized in a manner that would allow a patient to compare physicians or hospitals, search for a particular physician or hospital by geographic area or other criteria, or verify a physician's or hospital's certifications and licensures.

It is with respect to these and other considerations that the present invention has been made. Although specific problems have been addressed in this Background, this disclosure is not intended in any way to be limited to solving those specific problems.

SUMMARY

Embodiments of the present invention generally relate to providing an Internet-based system, involving a database and search capabilities and manipulations, to direct patients to potential healthcare providers, e.g., physicians, hospitals, nursing homes, treatment facilities, etc., and, similarly, to enable such providers to reach patients they may not otherwise reach. Aspects of particular embodiments relate to performing searches for healthcare providers based on geographic area, specialty, and/or other criteria, in which the company maintaining and/or managing the Web site (hereinafter, "the company") compiles and produces a results list of providers meeting such criteria. For example, a company Web site which provides such information and services is www.HealthGrades.com, provided by HealthGrades, Inc. From this list, a patient may access a detailed "report" or, in one embodiment, comparison ratings on that particular provider. In an embodiment, each report contains information which has been verified by the company or by another independent third party. In one embodiment, searches by a potential patient may be conducted from within the Web site of the company providing the healthcare provider information and comparison service, while other embodiments involve the use of common search engines external to the company Web site, such as Google, Yahoo, etc. Some embodiments relate to searches for physicians, while others relate to searches for hospitals, nursing homes, or other types of healthcare providers or treatment facilities.

As discussed herein, an aspect of a particular embodiment relates to a database of physician-related information, wherefrom data is gathered and compiled into the form of a "report" and is made available to potential patients. Such reports contain different types of verified information for each physician within the database. In an exemplary embodiment, in response to a search query for a particular physician name conducted using a search engine external to the company Web site, the patient receives a Web-based "profile" of a selected physician matching, or closely matching, the entered search terms. A profile lists detailed information potentially available about that physician which may be obtained in the form of a report. One embodiment of the invention provides for a standard profile, which provides the physician's specialty and general location (city/state) and provides a hyperlink for the patient to purchase a report on that physician containing information verified in some manner, such as by the company or by another independent third party. Such verified information comprises board certifications, disciplinary action(s), if any, years since medical school, etc. In an embodiment, the standard report may also include a patient-provided information section, including patient experience surveys completed by other patients of the physician and a place where patients accessing the report may share their experiences with the physician.

Another embodiment relates to a "member" profile and "member enhanced" report for physicians who have paid a fee to the company managing the Web site. The fee paid by the member physicians allows such physicians to provide information in the report in addition to that provided in a standard report. The member profile provides details on the physician's area of specialty, philosophy, practice, office location address, etc., and a hyperlink to a free detailed member enhanced report. The enhanced nature of the profile and its hyperlink to a free report on that physician provides a competitive advantage to a member physician.

An aspect of a particular embodiment relates to the different levels of verified information available in each member physician's report, in which such information may include: (1) a physician-verified, or physician-provided, section including information the physician feels will help a patient choose him or her as a physician; (2) a company-verified section including information such as board certifications, medical school, internship, residency, disciplinary action(s), if any, etc.; and (3) a patient-provided information section, including patient experience surveys by other patients of the physician relating their past experiences with the physician.

As noted above, another embodiment, and aspects related thereto, involves profiles and reports containing similar content, formatting, hyperlinks, etc. for searches regarding hospitals, medical practices, nursing homes, and/or other treatment facilities.

In other embodiments, the present invention's Internet-based system and Web site relates generally to how this verified healthcare provider information may be accessed by patients using the search capabilities provided by the company's predetermined Web page. In one embodiment, as discussed above, a patient receives a profile of a physician following a search query by name for a particular physician. In other embodiments, such as those involving search criteria limited to city/state information, a patient will be presented with a list of physician names with hyperlinks to those physicians' individual reports. In one embodiment, the patient will be prompted to pay a fee to obtain a report for a non-member physician. In certain embodiments, subsequent reports may be less expensive following the patient's initial purchase. In other embodiments, the physician may pay an upfront fee to the company so that patients may access his or her reports for free. Thus, a patient is presented with a list of physicians wherein some have free reports and others must be purchased. Consequently, patients are likely driven to the physicians with the free reports. As yet another aspect of the invention, groups of physicians may advertise their particular practice and provide access to a free report on the practice as well as free individual reports on each physician.

In an embodiment, the architecture and content of the Web site, as well as the ability to index the same, allows for a high natural placement in search results based on general Internet searches, such as those done using Google, Yahoo, or other search engines.

These and various other features, as well as advantages, which characterize the present invention, will be apparent from a reading of the following detailed description and a review of the associated drawings. This Summary is provided to introduce a selection of concepts in a simplified form that are further described below in the Detailed Description. This Summary is not intended to identify key or essential features of the claimed subject matter, nor is it intended to be used in any way as to limit the scope of the claimed subject matter.

BRIEF DESCRIPTION OF THE DRAWINGS

FIG. 3B illustrates information contained within a non-member report, as opposed to the member-enhanced report illustrated in FIG. 3A, in accordance with an embodiment of the present invention.

DETAILED DESCRIPTION

Figure 1:
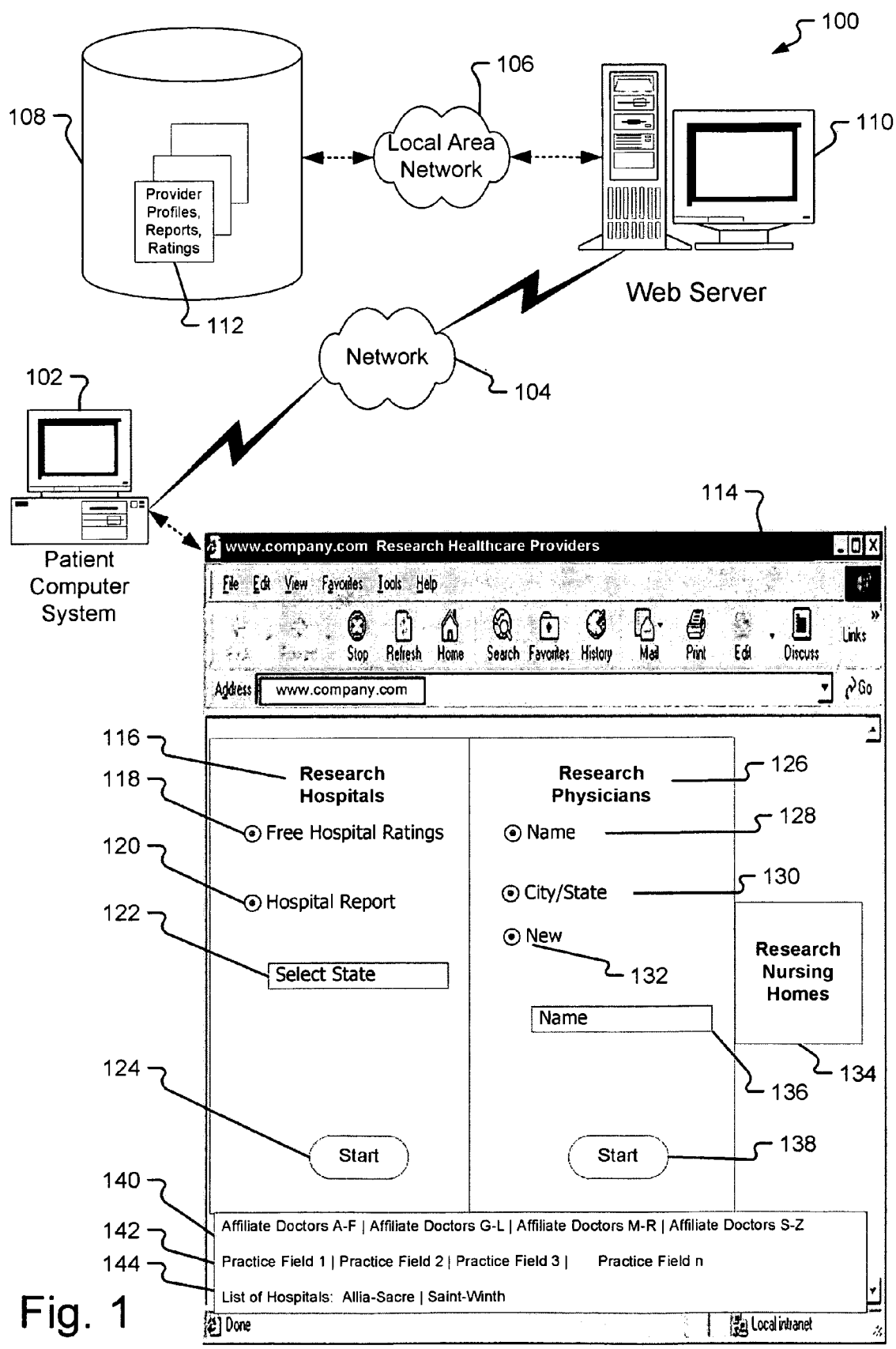
FIG. 1 illustrates a logical representation of a network environment for providing patients with the ability to research verified healthcare provider information through a search page on a company Web site in accordance with an embodiment of the present invention.

This disclosure will now more fully describe exemplary embodiments with reference to the accompanying drawings, in which the exemplary embodiments are shown. Other aspects may, however, be embodied in many different forms and the inclusion of specific embodiments in this disclosure should not be construed as limiting such aspects to the embodiments set forth herein. Rather, the embodiments depicted in the drawings are included to provide a disclosure that is thorough and complete and which fully conveys the intended scope to those skilled in the art. When referring to the figures, like structures and elements shown throughout are indicated with like reference numerals. Objects depicted in the figures that are covered by another object, as well as the reference annotations thereto, are shown using dashed lines. Optional steps or modules are also shown in a dashed-line format.

A network environment 100 for providing a potential patient with Web-based access to a system for obtaining verified information on healthcare providers, including comparison ratings amongst other data, is shown in FIG. 1. A "potential patient" or "patient" is any person seeking healthcare information and can thus be referred to by any term indicating such, including, but not limited to, user, consumer, etc. In an embodiment, the network environment 100 includes patient computer system 102 (hereinafter, "patient terminal"), a communication network 104 (hereinafter, "network"), a local area network 106, a database 108 storing healthcare provider information and data 112, a Web server 10, and a Web-based application, e.g., Web site, with a research Web page 114. While only one Web server 110 is shown, more than one server computer or separate servers, e.g., a server farm (not shown), may be used in accordance with an embodiment of the present invention. Further, although only one patient terminal 102 is shown, multiple patient terminals could communicate with Web server 110. The Web server 110, database 108, and healthcare provider information and data 112 are maintained by the company managing the Web site ("company"). The network environment 100 is not limited to any particular implementation and instead embodies any computing environment upon which the below-described functionality of the environment may be practiced.

In accordance with an embodiment of the invention, a patient may choose not to use a search engine, e.g., Google, Yahoo, etc., to search for healthcare provider information but, rather, may simply access the company's predetermined research Web page 114 that provides search capabilities on its database, such as database 108 shown in FIG. 1. In such an embodiment, patient terminal 102 receives research Web page 114 upon accessing the company Web site. (Other embodiments of the present invention relate to a patient's use of a search engine such as Google to research healthcare provider information. Such alternative embodiments are discussed below.) Research Web page 114 displays search prompts 116,126 and 134 for a patient to research hospitals, physicians, and/or nursing homes, respectively. To research a physician according to one embodiment of the invention, a patient may select buttons 128, 130, or 132, respectively, to search the physician by name, by city/state, or to find a new physician 132 for a desired specialty. After making the appropriate selection to research a physician, the patient may click on the Start button 138 to begin the search.

In another embodiment, a patient may research hospitals by selecting a search for free hospital ratings (button 118) or a hospital report (button 120). To begin the search, the patient may click on the Start button 124. In yet another embodiment, the patient may research nursing homes by selecting the Start button 134 for this type of search. Other embodiments provide for a patient to find a physician by selecting the specialty desired from a list 142 of such specialties or to select the physician's name or hospital name from an alphabetical index of such names for physicians (140) and for hospitals (144).

In accessing research Web page 114 in FIG. 1, patient terminal 102 accesses Web server 110 and receives the Web page from the company across a network 104. The network 104 may be any type of network conventionally known to those skilled in the art. In accordance with an exemplary embodiment, the network may be the global network (e.g., the Internet or World Wide Web). It may also be a local area network or a wide area network. While the network 104 may be any type of network conventionally known to those skilled in the art, the network 104 is described in accordance with an exemplary embodiment as the "World Wide Web, i.e., "Web" for short. As such, communications over the network 104 occur according to one or more standard packet-based formats, e.g., HTTP, HTTPS, H.323, IP, Ethernet, and/or ATM.

Figure 2A:
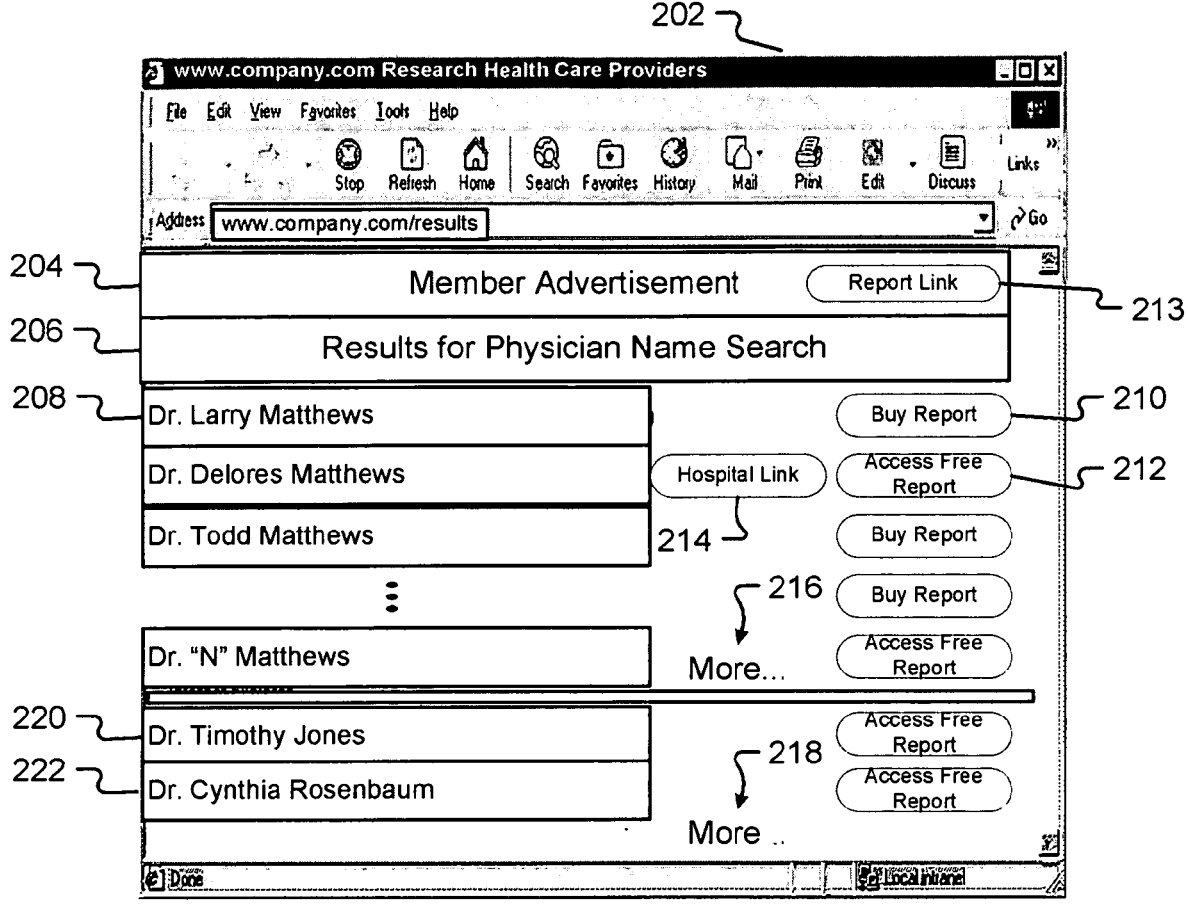
FIGS. 2A and 2B depict search results for a physician name search and a physician city/state search using the network environment and search Web page shown in FIG. 1, in accordance with an embodiment of the present invention.
Figure 2B:
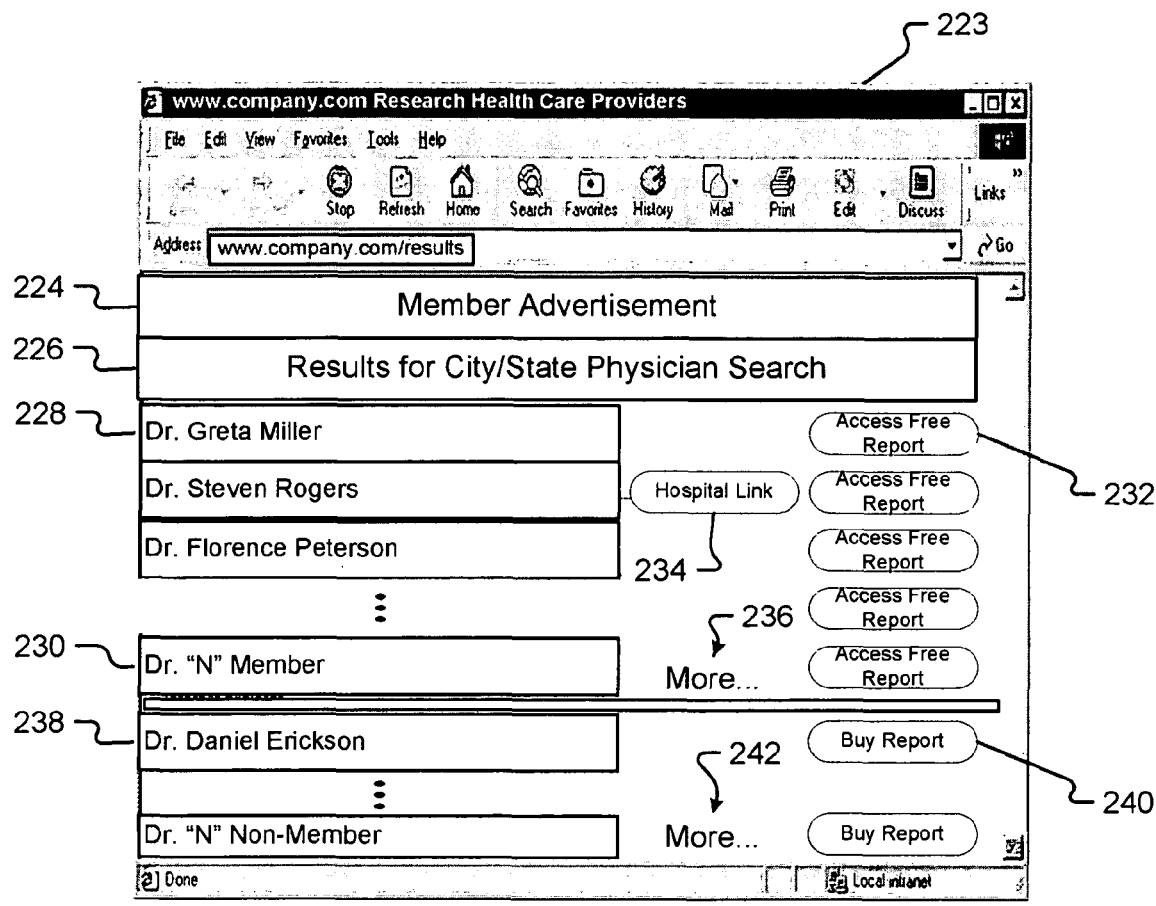

Turning now to a detailed illustration of the search results obtained after researching a physician as shown and discussed in reference to FIG. 1, a results list for a search by physician name and a results list for a search by city/state is shown in FIGS. 2A and 2B. In an embodiment, a physician search by name may produce a results page 202 with a results list 206 containing a section 208 with physicians satisfying the name, state, city, and specialty criteria specified by the patient, and a separate section 220 with "member" physicians 220 and 222 matching at least the state/city and/or specialty criteria ("member" status is discussed below).

In the exemplary embodiment depicted in FIG. 2A, each of the physicians listed in the first section 208 of results list 206 has the same last name, following a search for physicians by the name of "Matthews." Next to each physician name in the list 208 is a hyperlink 210 or 212 to access a report for that physician. These hyperlinks may indicate that the report may be purchased (210) in accordance with an aspect of one embodiment of the invention, or it may be accessed at no charge, i.e., for free (212), in accordance with another aspect. In an embodiment, a particular physician's report may be made available for free if he or she has paid an upfront fee to the company to make such reports available at no charge to patients accessing the site. The free nature of such reports creates a competitive advantage for the physicians offering them because patients can access their detailed information without having to pay a fee to the company.

In this disclosure, a physician paying an upfront fee to the company is referred to as a "member" physician; however, such a physician may be referred to by any term, such as an "affiliated physician," "associated physician," etc. According to another embodiment, the reports may be made free under another arrangement, such as, by way of example only, where the physician's practice group or affiliated hospital pays a fee to the company to make reports of all affiliated physicians available at no charge. Regardless of the entity or person paying the fee to the company, such physicians are referred to as "member" physicians for purposes of simplicity and consistency in this disclosure. As may be appreciated, the patient may be prompted to pay a fee when accessing a report, but the cost of such report(s) may be reduced if more than one, or, alternatively, a certain number of reports are purchased. Further, the patient may, in some embodiments, pay a flat fee for unlimited profiles. In yet other embodiments, the physicians may reimburse the costs of viewing their reports.

In addition to including a first list 208 of physicians that closely match the specific name criteria entered by the user, the physician name results Web page 202 also includes a separate section 220 of "member physicians" that closely match the specialty and city/state criteria, even though they may not match the name criteria input by the patient. For example, in the exemplary embodiment shown in FIG. 2A, the member physicians within the list 220 do not match the specified name criteria, but they do meet the state/city and/or specialty criteria specified. Because physicians within the list 220 are "member physicians," hyperlinks to free reports are provided next to their names. This feature gives member physicians a competitive advantage over other physicians by having their names appear on the results Web page 202 even if they do not meet the exact search criteria specified by the patient. In accordance with an embodiment of the invention, comparisons amongst the physicians may be provided to the patient, in which such comparisons highlight which physicians best fit the patient's specified criteria.

In an embodiment where the results are too numerous to list on one Web page, a hyperlink 216 to additional physicians satisfying the search results, or to additional "member physicians" closely matching the criteria (218), is included. In another embodiment, where a hospital pays a fee to the company, a hyperlink 214 to the hospital affiliated with a particular physician listed will also be provided next to that physician's name. In yet another embodiment, a member advertisement 204 for a practice group or hospital or other paying entity may be provided at the top of the results page. This advertisement 204 may be for a practice group or hospital closely related to the search criteria, or, in another embodiment, the advertisement may be for any member entity or physician. In an embodiment, the member advertisement may contain a hyperlink 213 for providing a report or ratings on that entity.

Where a patient conducts a search for a physician by city/state in accordance with an embodiment of this invention, results page 223 is displayed. In results page 223, a results list 226 contains section 228 listing "member" physicians satisfying the search criteria specified. Because these are member physicians, hyperlinks 232 to free reports are shown next to their names. In accordance with an embodiment where a hospital or medical practice is a member entity, a hospital hyperlink 234 for accessing a report or ratings on that hospital or medical practice is shown next to those physicians affiliated with the hospital. In separate section 238, non-member physicians meeting the search criteria are listed. Because these are non-members, hyperlinks 240 to purchase reports are provided.

As discussed with reference to results page 202, a member advertisement 224 is shown for results page 223 in accordance with an embodiment of this invention. Similarly, where additional physicians to those listed on the initial results page meet the search criteria, hyperlinks 236 and 242 provide access to such additional lists.

Figure 3A:
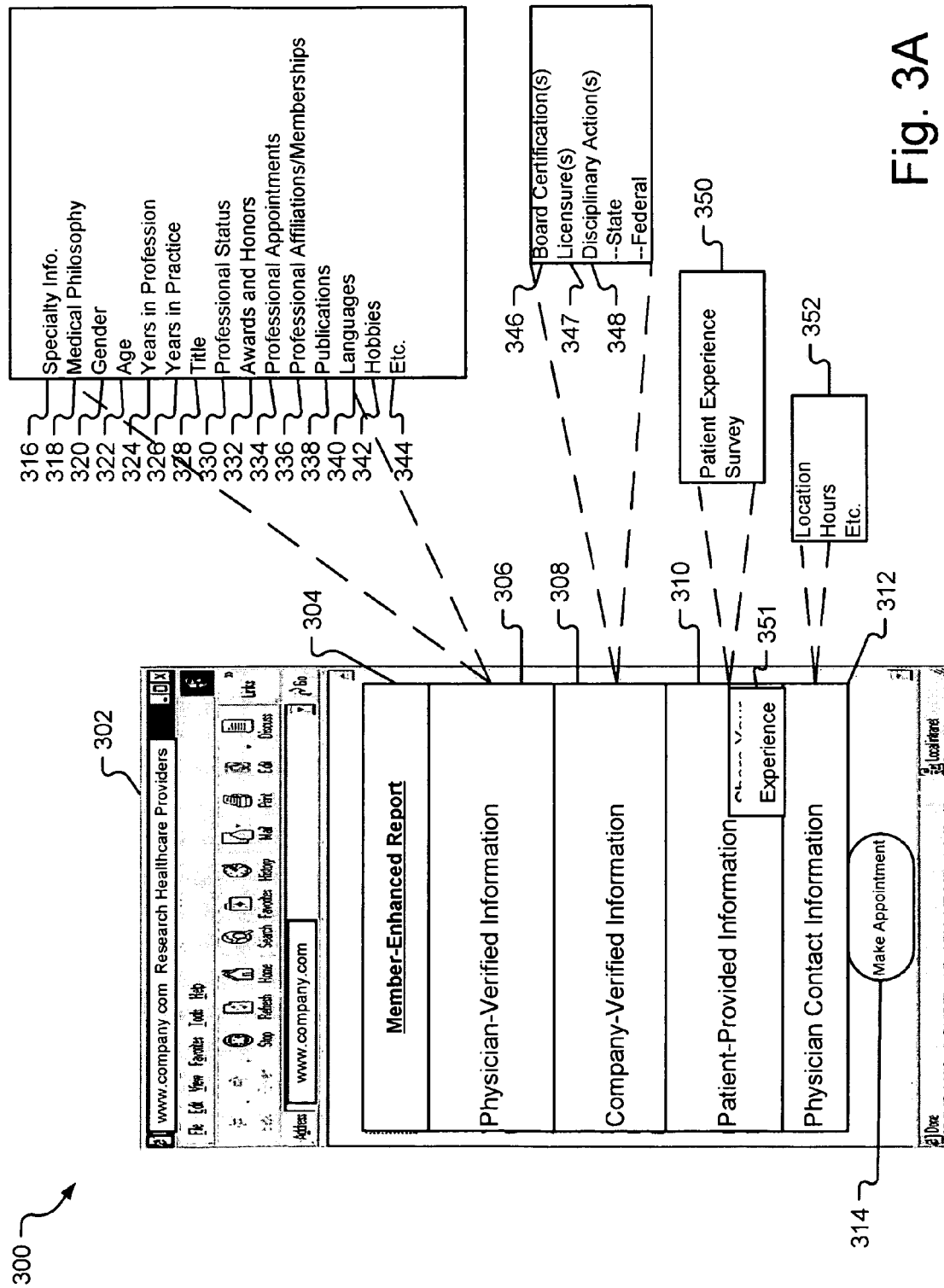
FIG. 3A illustrates detailed information that may be included in a physician member-enhanced report, which report may be obtained by selecting one of the physicians listed in the results page(s) depicted in FIG. 2, in accordance with an embodiment of the present invention.

A patient who selects to view a particular member physician's free report next receives a Web page view 302 of this member-enhanced report 304, as depicted in FIG. 3A. In an exemplary embodiment, the report 304 contains four sections, two of which contain verified information. The first section 306 contains physician-verified information, in which the member physician provides personal information, such as specialty information 316, medical philosophy 318, gender 320, age 322, years in the profession 324, years in the particular practice listed 326, if any, title 328, professional status 330, awards and honors 332, professional appointments 334, professional affiliations/memberships 336, publications 338, languages 340, hobbies 342, etc. 344. In essence, the member physician has the ability to craft some of the information provided to the patient. This information may or may not be verified by an independent third party, such as the company managing the Web site, but it is expected that the physician, at least, verifies this information.

The second section 308 comprises information preferably verified by an independent third party, such as the company managing the Web site, e.g., HealthGrades, Inc., regarding the physician's experience and training, such as board certification(s) 346, licensure(s) 347, and any and/or all disciplinary actions 348, both state and federal, to date or within a certain time period. In one embodiment, such verification may be expressly noted in the report 304. In essence, the verification of this information provides a potential patient with some assurance that the qualifications of the doctor have been checked by someone. In addition to verifications of board certifications and disciplinary actions, an embodiment may include verifications which also relate to the physician's medical school(s), internship, residency, fellowship information, etc. In another embodiment, the verification information may also include performance information, such as number of procedures performed, important dates, etc.

Turning now to the third section 310 of the report 304, the included information relates to patient-provided information and, preferably, relates to information that has been provided by past or current patients of the particular healthcare provider. In one embodiment, a patient experience survey 350 by current or former patients of the particular physician may be available. This may further include national averages based on certain predetermined questions conducted through surveys, as shown and discussed in reference to FIG. 4 below. By providing this information, the potential patient can view past performance of a particular doctor through another past or current patient's eyes. In another embodiment related to this section, the patient accessing the report may click the button 351 to rate the physician (or other healthcare physician) if he or she is currently, or has previously been, a patient of that physician (or other healthcare provider).

The fourth section 312 of the report 304 preferably comprises contact information 352 for the physician, which, by way of example only, may include location information, phone numbers, affiliated hospitals, health plans or other insurance information, hours, etc. Additionally, in some embodiments, a hyperlink 314 may be provided to allow the patient to directly access an appointment module from the report page 302. The patient may set an appointment directly from the appointment module (314).

While four sections are shown and discussed in reference to the member-enhanced report 304, it is conceivable that the report could contain numerous additional possible sections. Further, while this disclosure has listed specific types of information and data available in the report 304 in accordance with an embodiment of the invention, other embodiments of the invention may include other types of information and/or data. Moreover, other embodiments may have a different ordering of the sections. The exemplary embodiments depicted and discussed herein are not intended to limit the scope of the invention.

In contrast to the member enhanced report shown in FIG. 3A, a non-member report 354 within Web page 353 of FIG. 3B does not include an appointment module in accordance with one embodiment of the invention. In an embodiment, non-member report 354 lists the physician's name and/or medical specialty 356, location(s) and/or phone number(s) 358, gender 360, professional misconduct 362, if any, area hospital ratings 364, patient survey 366, and comparisons 368 to national and specialty averages. The comparison 368 to averages allows patients to differentiate among healthcare providers, and represents a particular benefit of the company Web site.

Figure 4:
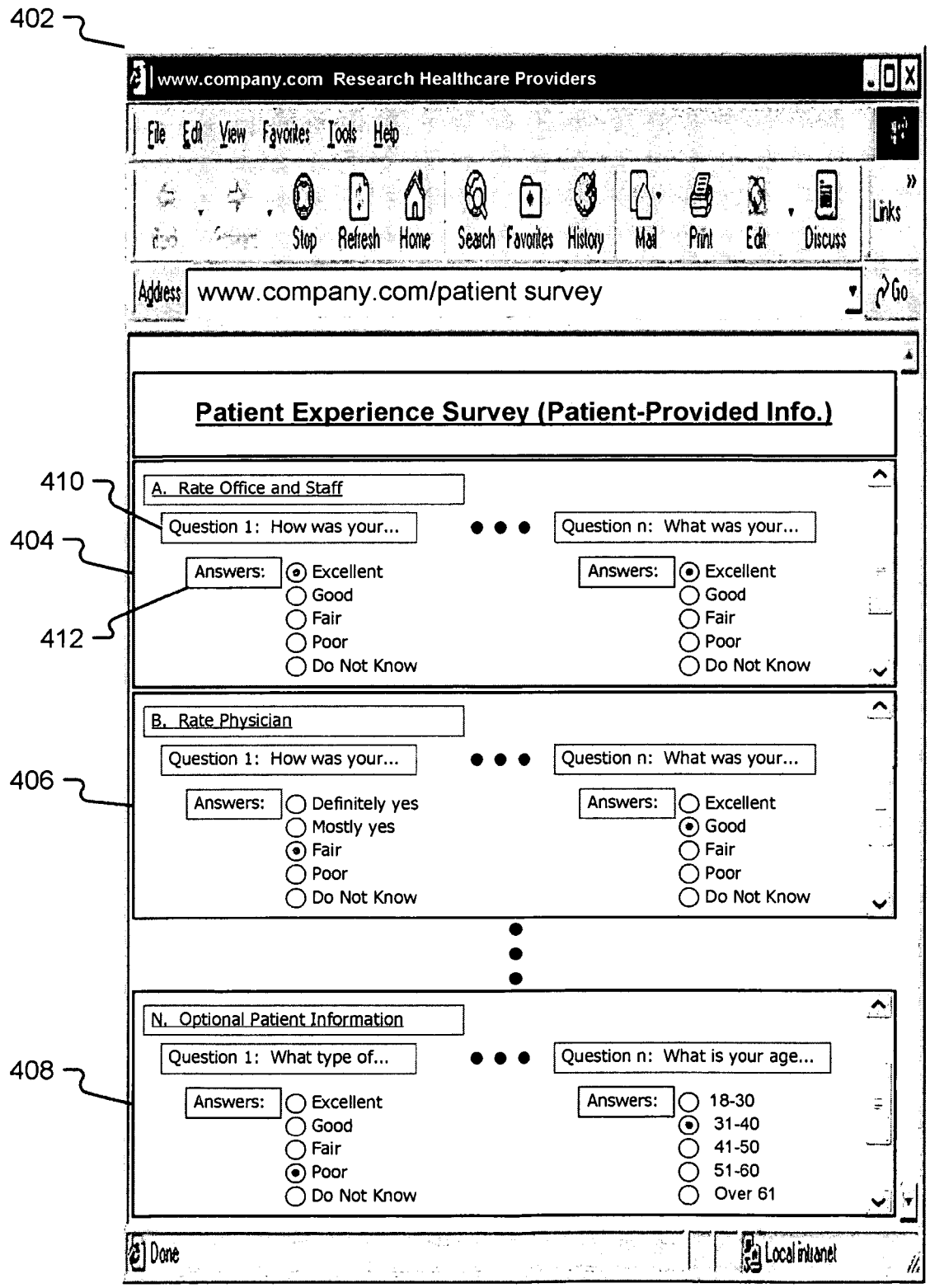
FIG. 4 depicts an on-line patient survey from which survey answers are used for compiling patient experience information provided in the patient experience section of a report such as that shown in FIG. 3A, in accordance with an embodiment of the present invention.

The patient-provided information 310 and 350 discussed above with respect to FIG. 3A is illustrated in patient experience survey 402 in FIG. 4. In accordance with an exemplary embodiment of the invention, the patient experience survey 402 has three separate sections, including a first section 404 where the patient is asked to rate the physician's office and staff. By way of example only, questions 410 relating to such ratings include: "Ease of scheduling urgent appointments;" "Office Environment;" "Friendliness and courtesy of the office staff;" and "Once you arrive for a scheduled appointment, how long do you have to wait (including waiting room and exam room) before you see this physician?" The patient is provided with a series of multiple choice answers 412 with which to answer the questions.

A second section 406 relates to questions asking the patient to rate the physician. By way of example only, questions relating to such may include: "Do you feel the physician spends an appropriate amount of time with you?"; "Does the physician listen to you and answer your questions?"; "Does the physician help you understand your medical condition(s)?"; "Do you trust your physician to make decisions/recommendations that are in your best interests?"; "Would you recommend your physician to family/friends?"; and "How many visits have you had with this physician within the last two years?"

Referring to the third section 408 depicted in the exemplary embodiment of FIG. 4, the patient may answer multiple choice questions regarding optional personal information. By way of example only, such questions include: "What type of health insurance do you have?"; "What is your gender?"; "What is your age?"; "What is your current marital status?"; "Which category best describes you?"; "What is the highest level of school you have completed?"; and "What is your annual household income?"

Figure 5A:
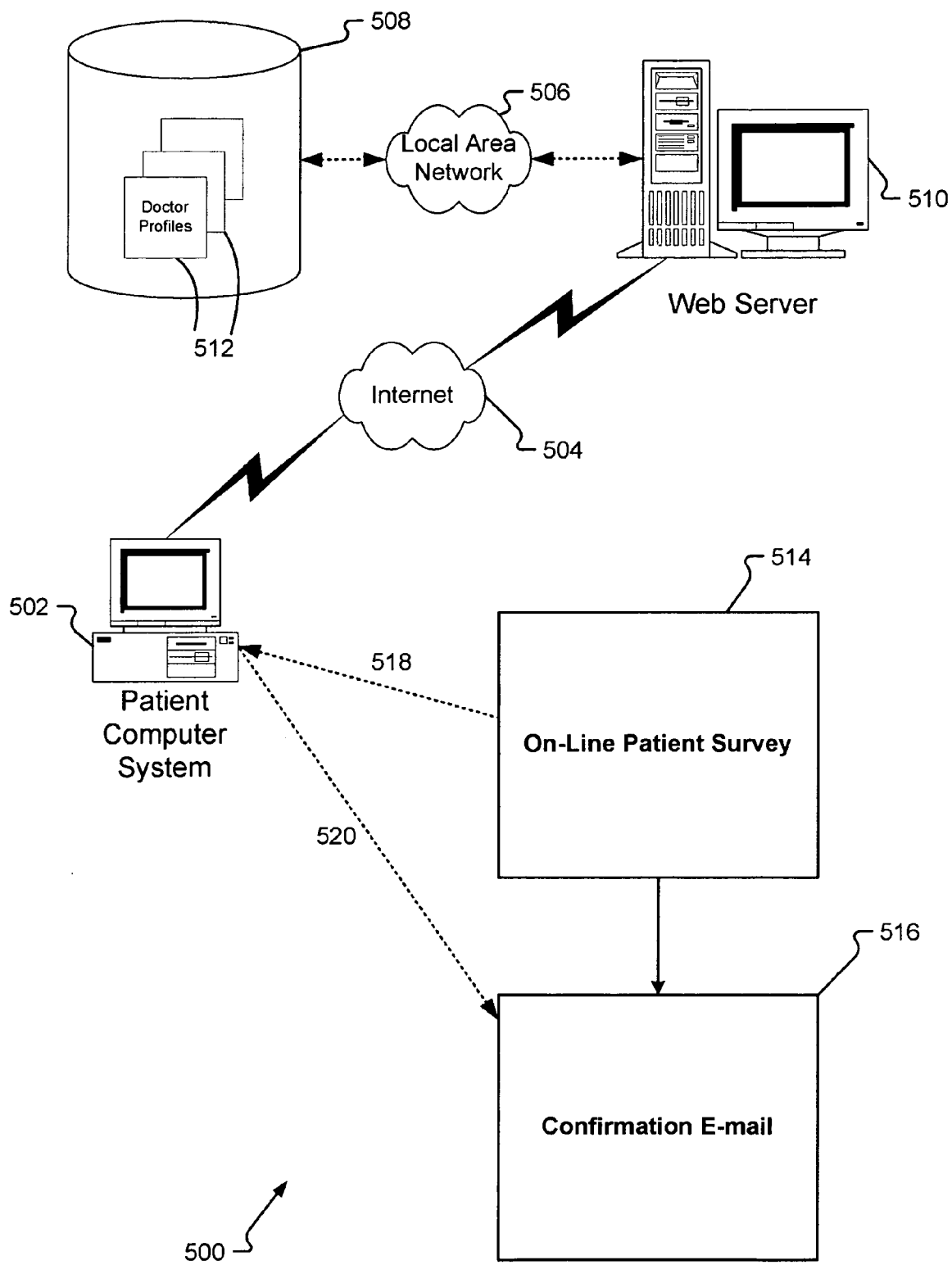
FIG. 5A is a representation of a patient verification system for completing the past or current patient experience survey shown in FIG. 4 in accordance with an embodiment of the present invention. The operation flow of the process for collecting data and information through the use of such surveys is shown in FIG. 5B. Further, the operation flow of verifying that such data or information is from actual current or past patients of the particular healthcare provider being rated is shown in FIG. 5C in accordance with an embodiment of the present invention.

To verify that the patient-provided information in patient survey 402 is given by specific individuals and, preferably, those who have been actual patients of the physician being rated, FIG. 5A shows a system for confirming the e-mail address of the patient completing the survey. After completing an on-line patient survey 514, the patient computer system 502 receives a confirmation e-mail 516. If the company Web server determines that the e-mail confirmation was successfully transmitted, the Web server will then proceed with steps known to those of ordinary skill in the art for compiling such information and data with relevant data already stored in the company database. An optional feature would permit the company to limit the number of surveys completed by a particular past or current patient in a predetermined time period.

Figure 5B:
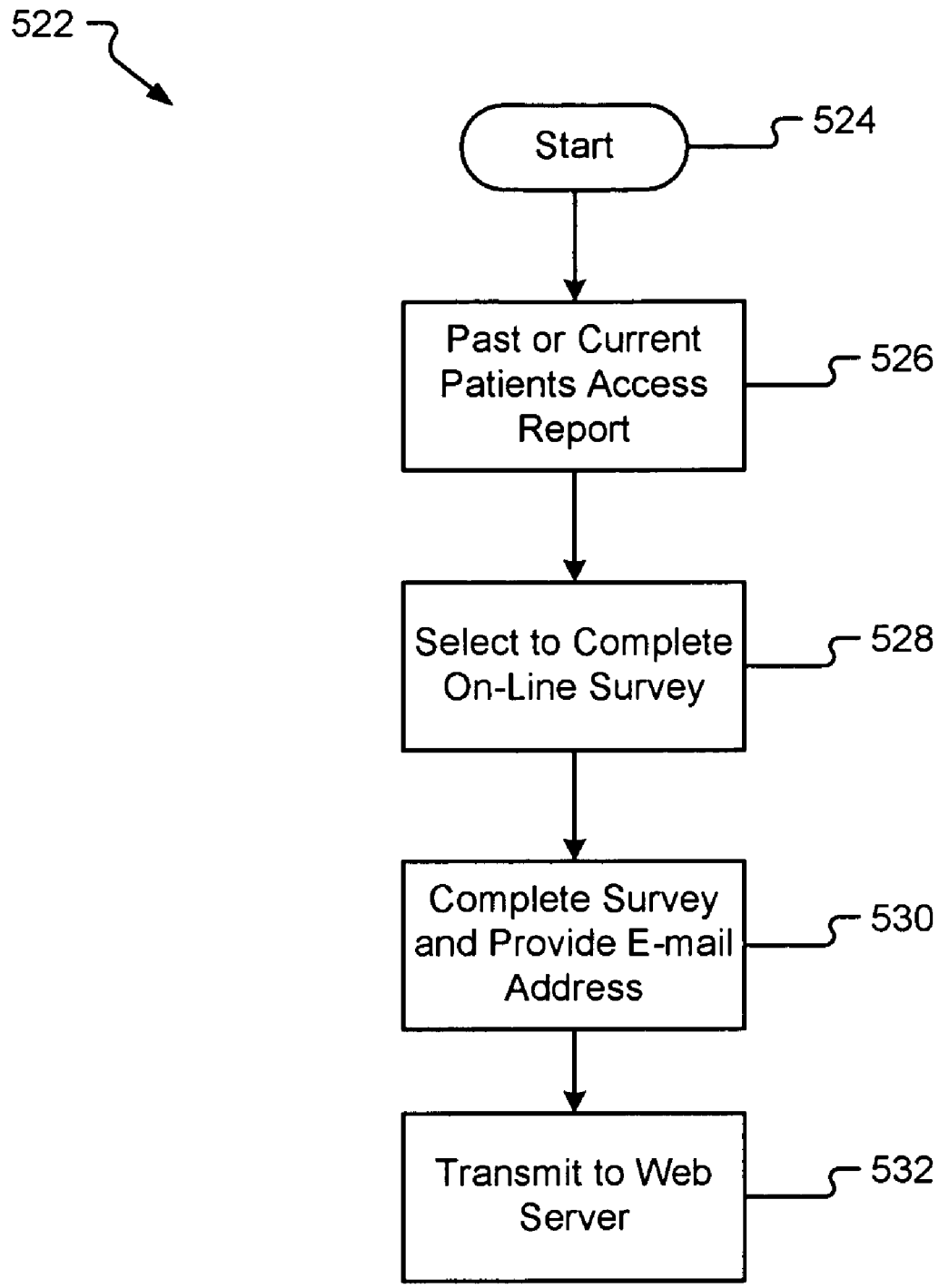

Turning to FIG. 5B, a process 522 is shown for collecting information from past or current patients of a particular healthcare provider in accordance with an embodiment of the present disclosure. Start operation 524 is initiated following a past or current patient's access of the company Web server 100 and the transmittal of research Web page 114 to the patient terminal 102. From the start operation 524, process 522 proceeds to access report operation 526, in which the past or current patient accesses a report of a particular healthcare provider. Next, in select operation 528, the past or current patient selects to complete an on-line survey from within the provider report. Once the past or current patient has completed the survey and provided an e-mail address in operation 530, the survey is transmitted to the company web server in transmit operation 532.

Figure 5C:
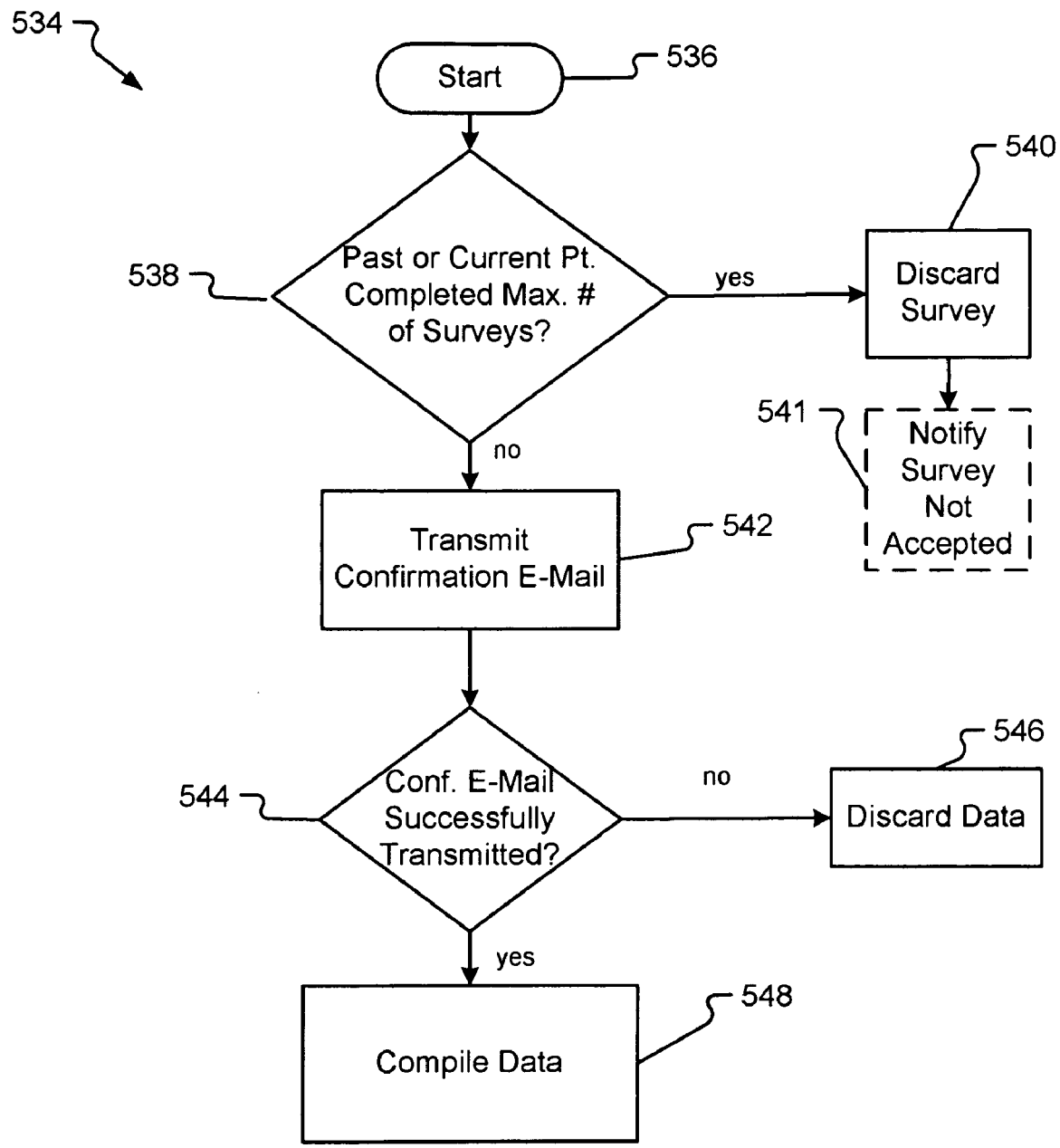

With respect to FIG. 5C, a process 534 for compiling data from the on-line patient survey 514 and verifying that such survey has been completed by an actual past or current patient of the particular healthcare provider being rated is shown in accordance with an embodiment of the present invention. Start operation 536 is initiated following the company Web server's receipt of the past or current patient's on-line survey. Next, the operation flow of process 534 proceeds to query operation 538. Query operation 538 determines whether the past or current patient has already completed the maximum number of surveys permitted by the company for that particular healthcare provider. If the maximum number of surveys has been reached, flow branches YES to discard survey operation 540. As an optional step, the company may transmit a notice to the past or current patient indicating that the survey was not accepted in notify operation 541. Because this step is optional, it is shown in dashed-lines format. If the maximum number of surveys has not been met, flow branches NO to transmit confirmation e-mail operation 542, in which the company transmits an e-mail to the e-mail address provided by the past or current patient. From transmit operation 542, process 534 proceeds to query operation 544, in which operation 544 determines whether the confirmation e-mail was successfully transmitted. A successful transmittal would indicate to the company that a valid e-mail address was given by the past or current patient. If the confirmation e-mail was not successfully transmitted, flow branches NO to discard data operation 546, in which the company discards the on-line survey provided by that particular past or current patient. If the confirmation e-mail is successfully transmitted, flow branches YES to compile data operation 548, in which the information and data provided by the patient survey is compiled with other data provided by other past or current patients and maintained within the company database.

Figure 6:
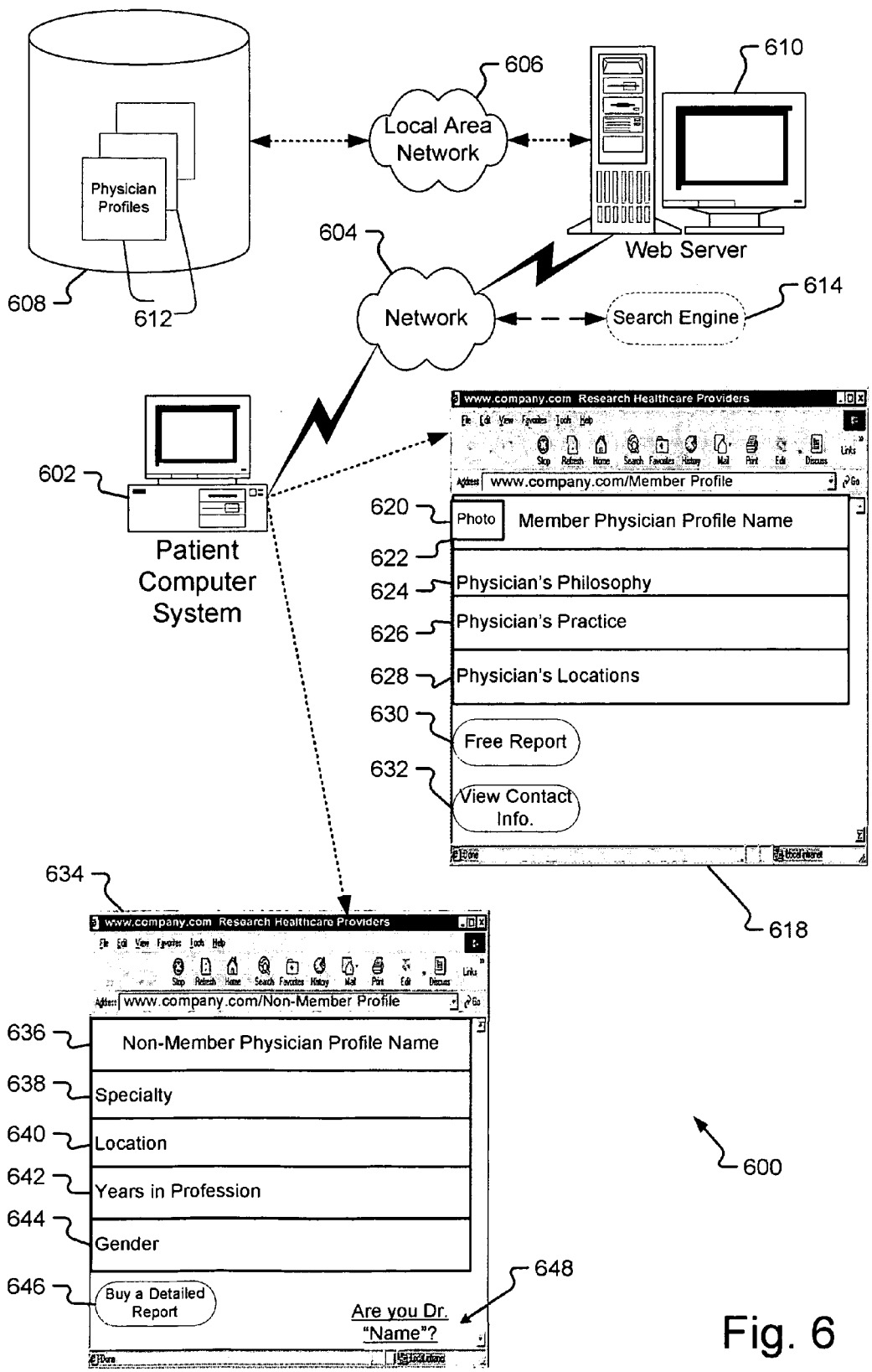
FIG. 6 depicts the logical representation of a patient search for a physician by name using a typical search engine external to the company Web site in accordance with an embodiment of the present invention.

While in an embodiment of the invention, a patient may directly access the company Web site to research and obtain verified information regarding a healthcare provider, in a further embodiment (shown in FIG. 6) a patient may also search for a particular healthcare provider through use of a search engine 614, such as, by way of example only, Google, Yahoo, etc. In such an embodiment, a patient will likely enter search terms including the physician's name and title. Upon receiving this information, the company Web server 610 will access a physician profile 612 from database 608 across local area network 606. The physician profile 612 is then transmitted across the network 604 to patient computer system 602. In accordance with embodiments of the invention, there are multiple types of physician profiles. For example, a member profile or a non-member physician profile are available; however, other types may be possible as well. In embodiments, a profile contains abbreviated information regarding the physician. In some embodiments, headings of information available in a report are included in a profile. The type of physician profile transmitted to the patient depends on whether the physician for whom the search is conducted is a member physician or not. Where the physician is a member, a member physician profile 618 will be transmitted to the patient. Because the physician in profile 618 is a member, he or she will likely have supplied his or her photo to the company, and, in an embodiment, this photo 620 may be included in the profile along with the physician's name 622. Further, because a member physician has provided information and/or verified such to the company, the physician's philosophy 624 (including specialty information in some embodiments) is included in the profile, as well as a description of the physician's practice 626 and office locations 628, etc. Additionally, a hyperlink 630 to a free report and a second hyperlink 632 to contact information are included in the member physician profile.

On the other hand, a non-member physician profile 634 includes a hyperlink for purchasing a report 646. In profile 634, the physician's name 636, specialty 638, location 640, years in profession 642, and gender 644 are provided. Also, in furtherance of the company Web service's marketing efforts, a hyperlink asking "Are you Dr. _____" 648 is included. Hyperlink 648 gives physicians accessing the Web site the opportunity to become members of the service and provide detailed information to patients accessing the site.

Figure 7A:
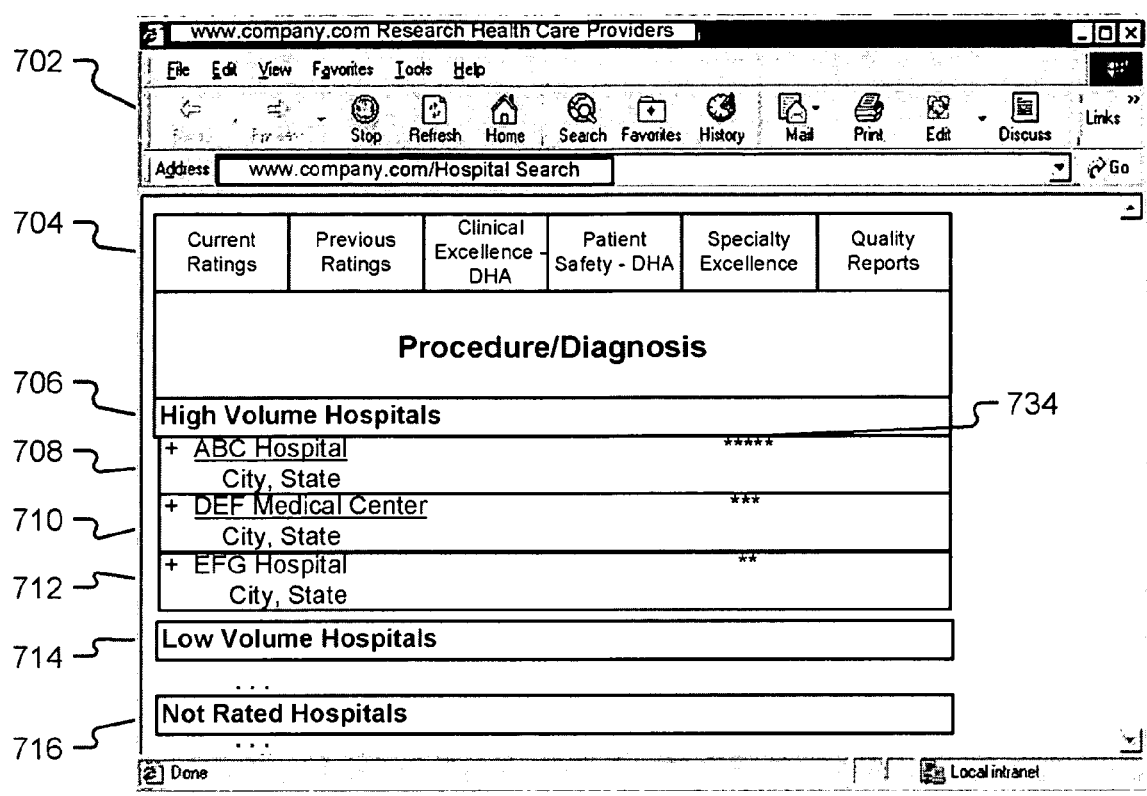
FIGS. 7A and 7B illustrate an embodiment of the invention shown in FIG. 1 depicting hospital ratings and a hospital report which may be obtained by a patient after conducting a search on the company Web page shown in FIG. 1.
Figure 7B:
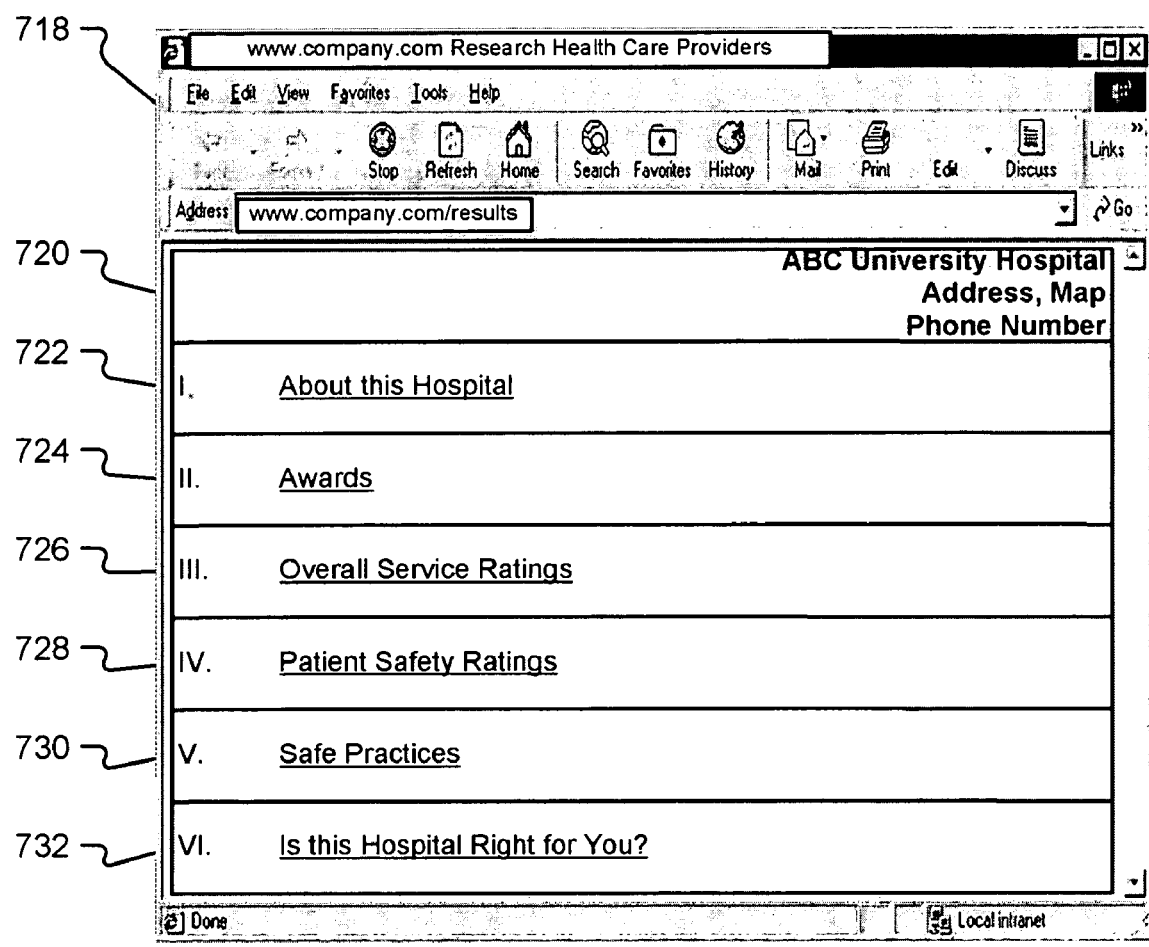

While this discussion has focused in large part on physician searches, FIGS. 7A and 7B show the ratings and reports available for hospitals in accordance with embodiments of this invention. While the term "hospital" is used in these figures and discussion, any type of treatment facility, e.g., medical practice, treatment center, etc. could be considered in accordance with embodiments of this invention. Hospital ratings Web page 702 in FIG. 7A provides the hospital ratings for specific hospitals based on search criteria entered by the patient. In specifying criteria, the patient is required either to specify a procedure/diagnosis or a type of award received by the preferred hospital. The ratings are grouped into high volume hospitals 706, low volume hospitals 714 and hospitals not rated 716. In an exemplary embodiment, hospitals 708, 710 and 712 are listed with their city/state information. The ratings 734 given to these hospitals are also shown in accordance with an exemplary embodiment of the invention. Any type of rating or scoring system could be used in embodiments of the invention. From the button bar 704 on the hospital ratings Web page 702, a patient may access current ratings, previous ratings, clinical excellence-Distinguished Hospital Award ("DHA") information, patient safety-DHA information, specialty excellence, and/or quality reports, etc. 704.

In accordance with an embodiment of the invention, a patient may access the detailed information report 718 in FIG. 7B for a hospital by selecting the quality report hyperlink on the hospital ratings Web page 702 (FIG. 7A). In other embodiments, this quality report for a particular hospital may also be accessed through a search 120 for such a report as shown in FIG. 1. The hospital report may be purchased or delivered free to the patient depending on whether the hospital has paid an upfront member fee to the company, as discussed above with regard to member physicians. Regardless of how this report is accessed, the detailed information report 718 shows an exemplary embodiment of the report for hospital name 720. This report includes information about the hospital (722), awards the hospital has received (724), if any, overall service ratings for the hospital (726), patient safety ratings (728), safe practices (730), and information (732) for assisting a potential patient with determining whether this hospital is right for him or her.

Figure 8:
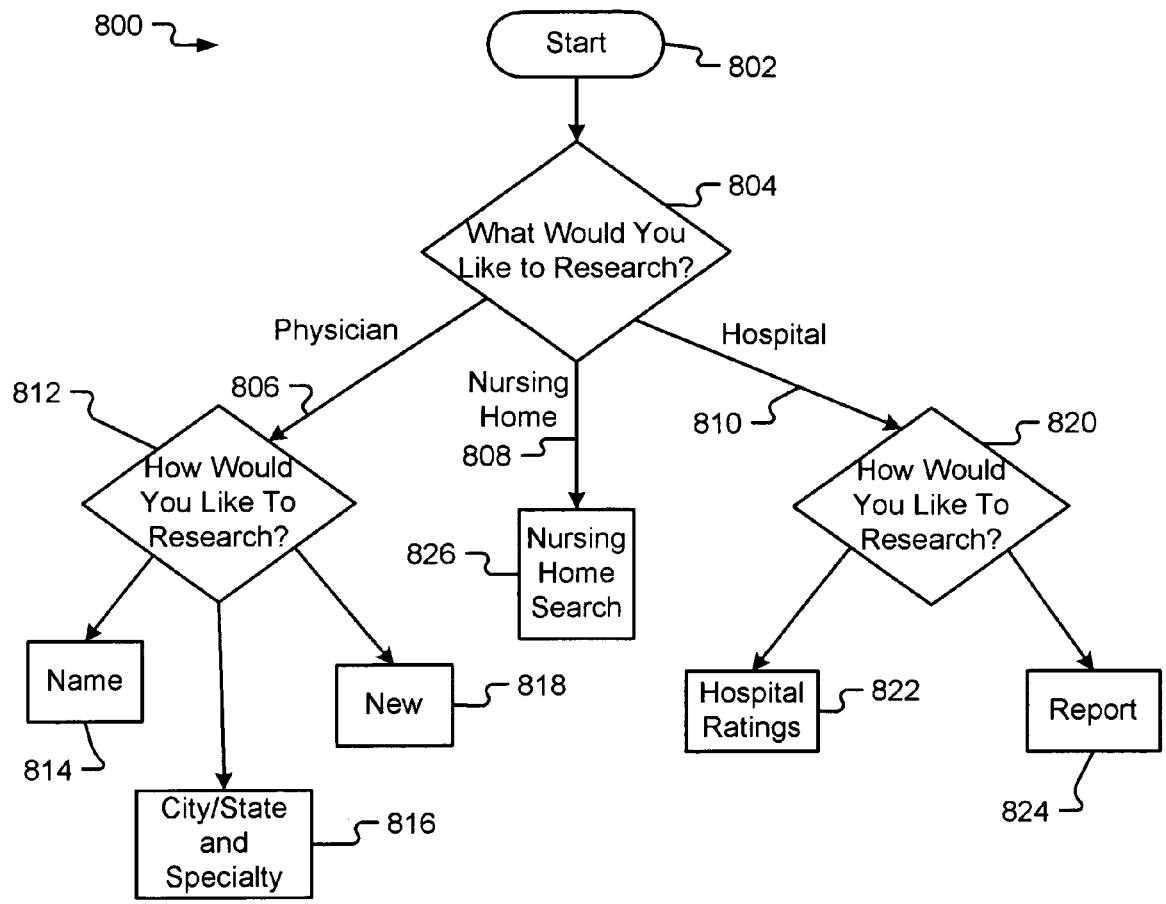
FIG. 8 is a flow diagram illustrating operational characteristics of a search performed for a physician or hospital using the company research Web page depicted in FIG. 1 in accordance with an embodiment of the present invention.

With respect to FIG. 8, a process 800 for researching healthcare provider information is shown in accordance with an embodiment of the present disclosure. Start operation 802 is initiated following patient access of the company Web server 110 and the transmittal of research Web page 114 to the patient terminal 102. From the start operation 802, the operation flow of process 800 proceeds to query operation 804. Query operation 804 determines whether the patient would like to research physicians 806, nursing homes 808, or hospitals 810. If the patient selects to research physicians 806, flow branches to physician query operation 812, wherein query 812 determines whether the patient would like to search for physicians by name 814, by city/state and specialty 816, or for a new physician 818. On the other hand, if the patient selects to research hospitals 810, flow branches to hospital query operation 820, wherein query 820 determines whether the patient would like to research hospitals by evaluating ratings 822 of hospitals meeting specified criteria, or by receiving a hospital report 824. If the patient selects to research nursing homes 808, flow branches to nursing home search 826. In accordance with other embodiments of the invention, the company Web service may provide additional search scenarios and types of healthcare providers and related entities for which to search.

Figure 9:
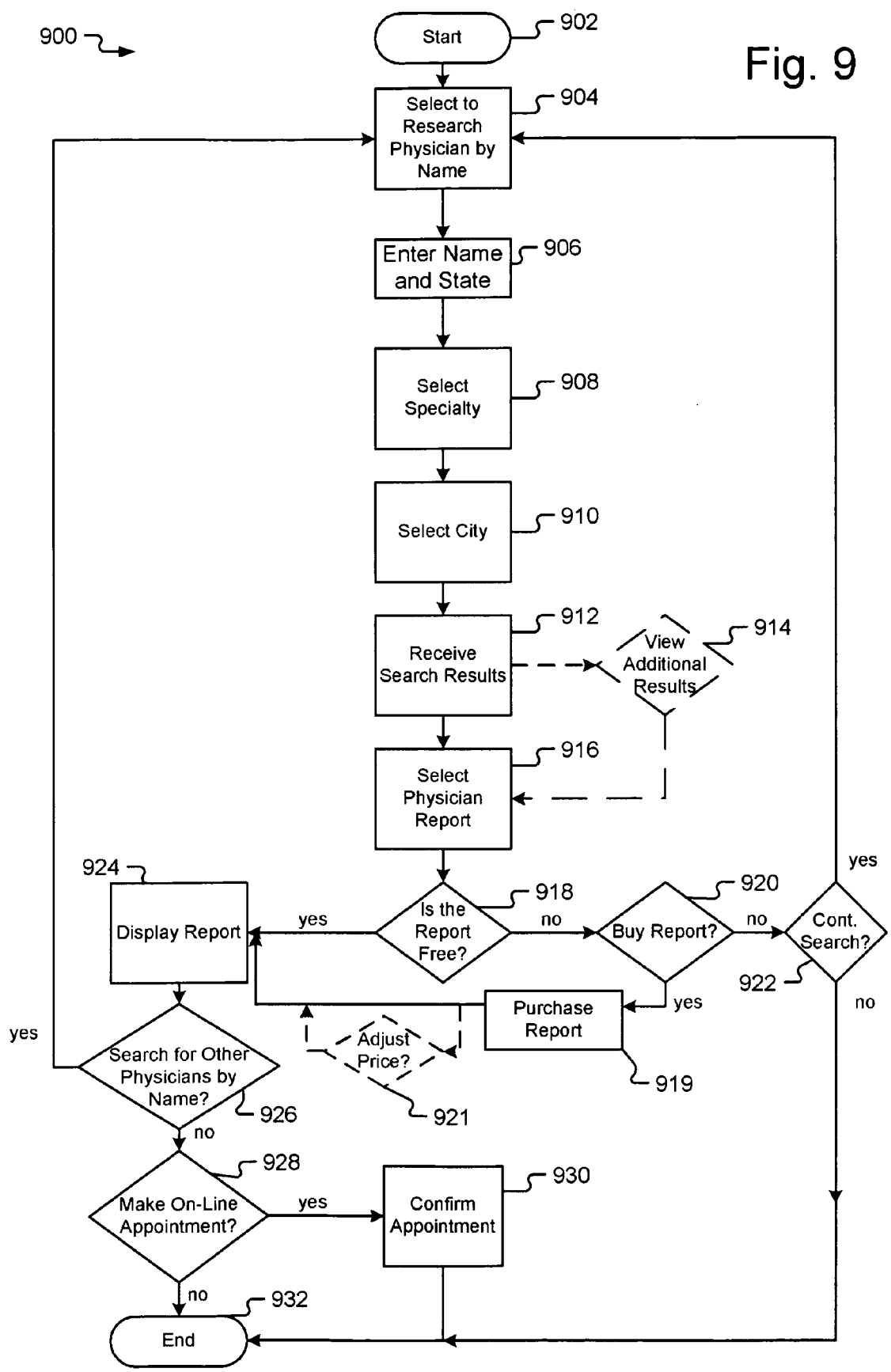
FIG. 9 is a flow diagram illustrating operational characteristics of a search performed for a physician by name using the predetermined Web page providing search capabilities on the company's database shown in FIG. 1, in accordance with an embodiment of the present invention.

Turning now to FIG. 9, a process 900 for researching a physician by name, as shown in step 814 in FIG. 8, is shown in accordance with an embodiment of the present disclosure. Operation flow 900 begins with start operation 902 which is initiated following the patient's access of research Web page 114. From start operation 902, the operation flow of process 900 proceeds to operation 904 where a user selects to research physicians by name. Next, the patient is prompted to enter the name and state desired in input operation 906. The patient is then prompted to select a specialty in operation 908 and a city in operation 910. Next, the operation flow of process 900 proceeds to operation 912 where search results are received. Receive operation 912 receives the search results based on the criteria specified in the preceding steps. The patient may either select a physician report 916 or may first view additional results 914, if any are available. Upon selecting a physician report 916, the flow proceeds to query operation 918. Query operation 918 determines whether a free report is available. If query operation 918 determines that a free report exists, flow branches YES to display report 924. After reviewing the report, the flow proceeds to search query 926 to determine whether the patient would like to search for other physicians by name. If search query 926 determines that the patient would like to proceed with another search, flow branches YES to research operation 904. On the other hand, if search query 926 determines that the patient would not like to conduct any further searches by name, flow branches NO to make on-line appointment query 928. If the patient would like to make an appointment with the physician, flow branches YES to confirm appointment operation 930. If the patient does not desire to make an appointment, flow branches NO to terminate operation 932 which ends research process 900. As one reasonably skilled in the art would understand, on-line appointment query 928 may occur before the search query 926.

If free report query 918 determines that a free report for the selected physician is not available, flow branches NO to buy report query 920. If buy report query 920 determines that the patient would like to purchase a report, flow branches YES to purchase report operation 919. As one reasonably skilled in the art would understand, interim steps may be involved in purchase report operation 919, i.e., involving entering of payment information, etc. In an embodiment of this invention, the payment amount may depend on whether the patient has previously accessed other reports and can thus receive a reduced price, etc. Thus, flow branches YES to purchase report operation 919 with an optional (shown in dashed-lines format) pricing adjustment query 921. Where no discounts are available, no price adjustments are made. On the other hand, if price discounts are available, the patient would pay a reduced price for a report in buy report query 920 in accordance with an embodiment of the invention. Following purchase report operation 919, flow proceeds to display report operation 924, in which the report is displayed. If query operation 920 determines that the patient does not desire to purchase a report, flow proceeds NO to search query 922, which determines whether the patient would like to search for other physicians by name. If the patient would like to search for more physicians by name, flow branches YES to select operation 904. If the patient does not desire to search for more physicians by name, flow branches NO to terminate operation 932, which ends research process 900.

Figure 10:
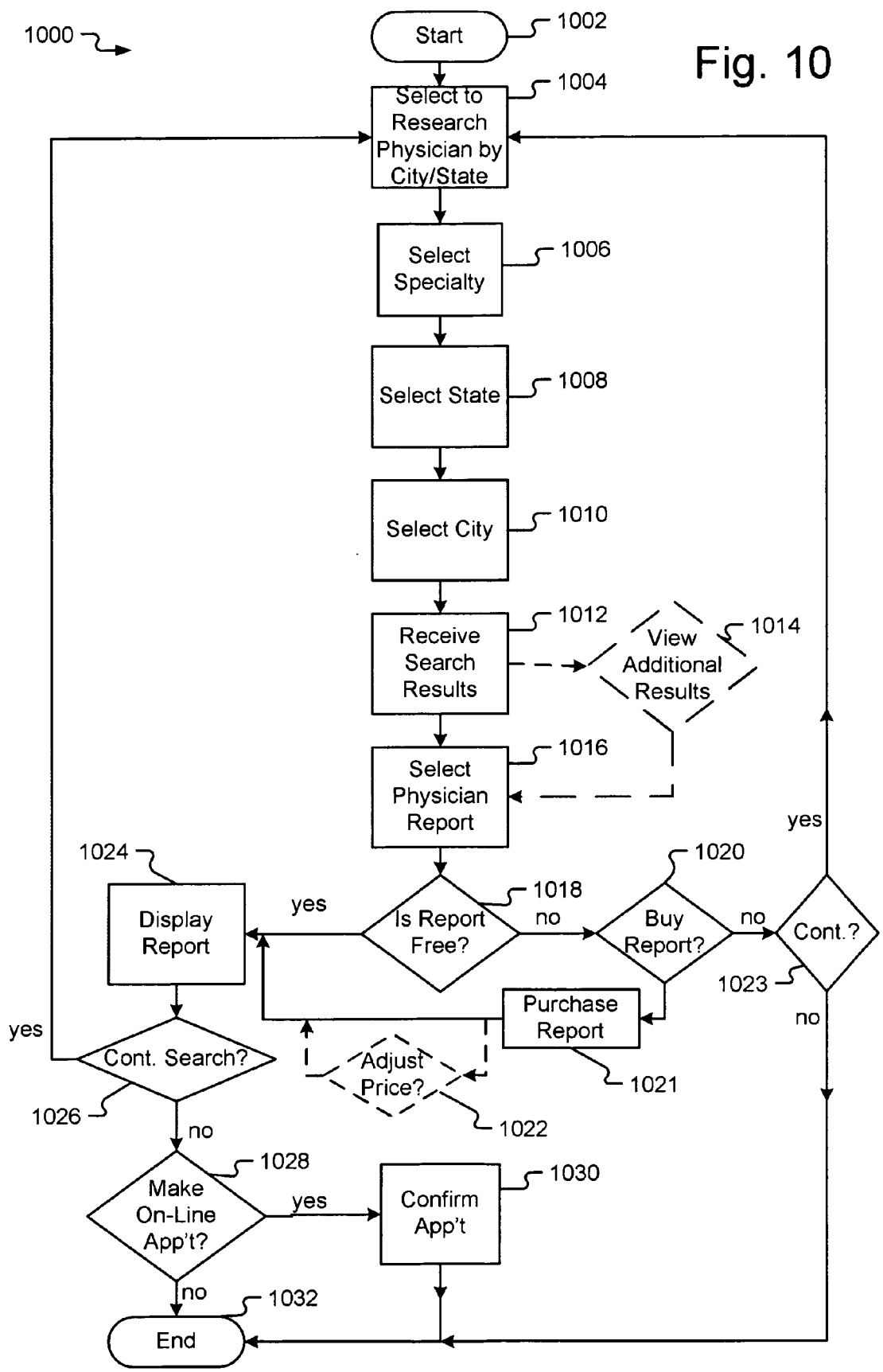
FIG. 10 is a flow diagram illustrating operational characteristics of a search performed for a physician by city/state criteria using the predetermined Web page providing search capabilities on the company's database shown in FIG. 1, in accordance with an embodiment of the present invention.

Turning now to FIG. 10, process 1000 is shown in accordance with exemplary embodiments of the present disclosure wherein the patient desires to research a physician by city/state and specialty criteria. Start operation 1002 is initiated in response to the patient's access of the research Web page 114. From start operation 1002, the patient selects to research a physician by city/state criteria in select operation 1004. The patient next selects a particular specialty, state, and city in operations 1006, 1008, and 1010, respectively. Following select operation 1010, the operation flow of process 1000 proceeds to operation 1012 where the search results are received. From here, the patient may select a physician report 1016 or may optionally view additional results 1014 before selecting a report 1016. After select physician report operation 1016, flow proceeds to query 1018 which determines whether a free report is available. The remaining operations and associated flow processes 1018-1032 are analogous to those described in reference to FIG. 9 for operations 918-932.

Figure 11:
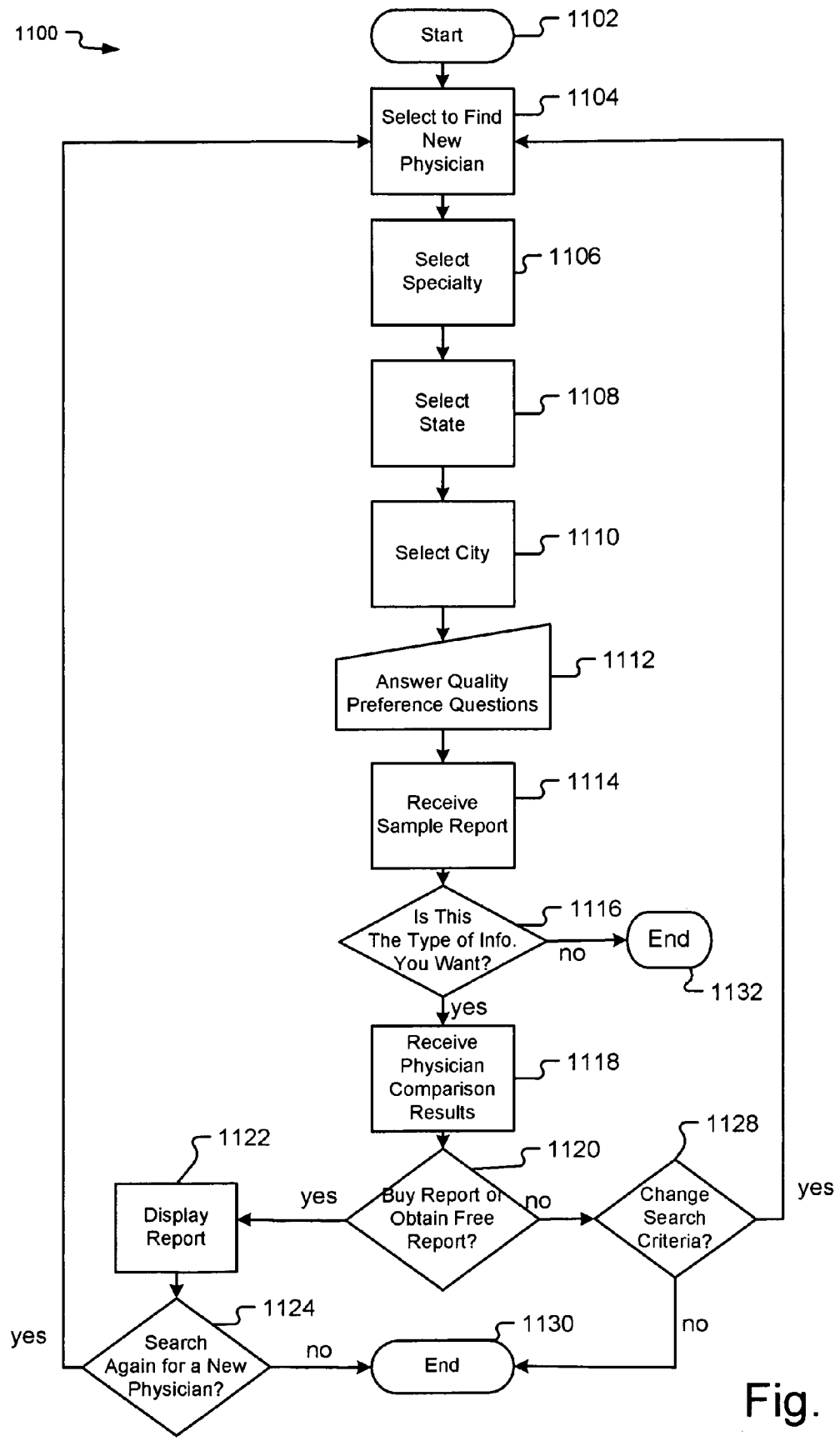
FIG. 11 is a flow diagram illustrating operational characteristics of a search performed for a new physician using the predetermined Web page providing search capabilities on the company's database shown in FIG. 1, in accordance with an embodiment of the present invention.

Referring now to FIG. 11, process 1100 for finding a new physician is shown in accordance with an embodiment of the present invention. Start operation 1102 begins process 1100 following the patient's accessing of research Web page 114. From start operation 1102, the patient selects to find a new physician in select operation 1104 and then selects a specialty, state, and city in operations 1106, 1108, and 1110, respectively. Following select operation 1110, the patient is asked to answer preference questions for the type of care desired, etc., in operation 1112. The operation flow 1100 then proceeds to operation 1114, which provides the patient with a sample report of the type of information which may be contained in a selected report. Next, query 1116 determines whether the patient would like to receive the type of information shown in the sample report. If not, flow branches NO to terminate operation 1132, which ends process 1100. If query 1116 determines that the patient would like to receive the type of information shown in the sample report, flow branches YES to receive operation 1118 where physician comparison results are provided. In particular, operation 1118 provides the patient with information regarding how well physicians listed satisfy the specified criteria 1106, 1108, and 1110.

Following receipt of the comparison results in operation 1118, flow proceeds to buy report query 1120. If query 1120 determines that the patient would not like to buy a report, or, alternatively in another embodiment, not desire to obtain a free report, flow proceeds NO to change search criteria query 1128, which allows the patient to provide different search criteria if so desired. If search criteria query 1128 determines that the patient would like to change the criteria specified, flow proceeds YES to find a new physician operation 1104. If the patient does not desire to change search criteria, flow proceeds NO to terminate operation 1130, which ends process 1100. If buy report query 1120 determines that the patient would like to buy a report, or if such a report is free in accordance with another embodiment, flow branches YES to display report operation 1122. From display report operation 1122, process 1100 proceeds to query 1124 where a user selects whether to search for other new physicians. If further searches are desired, flow branches YES to search for a new physician in operation 1104. Alternatively, flow branches NO to terminate operation 1130 if the patient does not desire to conduct further searches.

Figure 12:
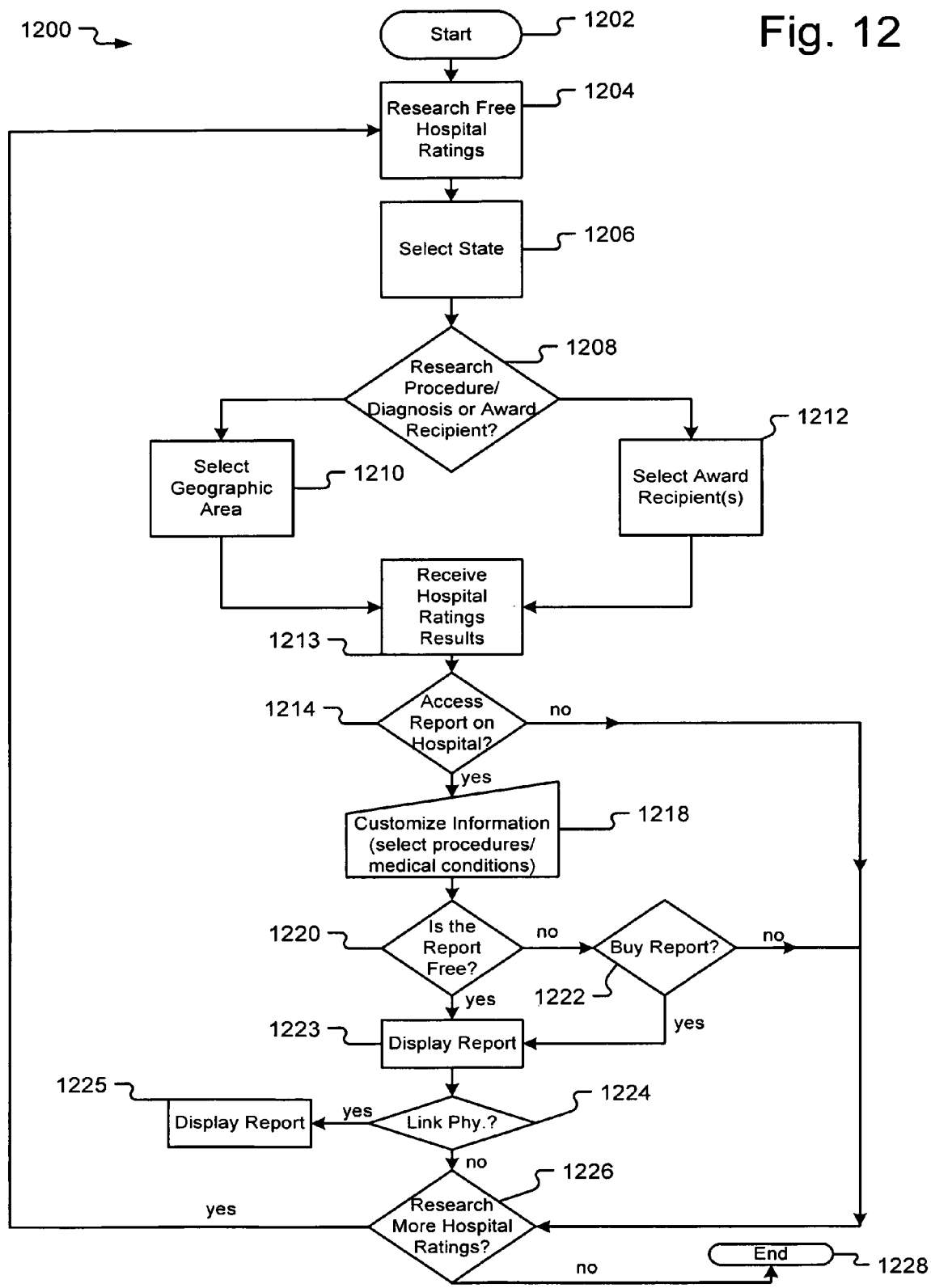
FIG. 12 is a flow diagram illustrating operational characteristics of a search performed for hospital ratings using the predetermined Web page providing search capabilities on the company's database shown in FIG. 1, in accordance with an embodiment of the present invention.

Turning to embodiments involving searches for hospital information, FIG. 12 shows process 1200, which is described in accordance with an exemplary embodiment as beginning with start operation 1202 following the patient's access of research Web page 114. From start operation 1202, the operation flow of process 1200 proceeds to research hospital ratings operation 1204. These ratings are made available free of charge in accordance with an embodiment of the present invention, but other embodiments may involve purchasing such ratings and related information. Next, the patient selects the desired state in operation 1206, and process 1200 flows to research query 1208, in which the patient selects whether to select a geographic area 1210 or award recipient(s) 1212. Following select operations 1210 or 1212, process 1200 proceeds to operation 1213 where hospital ratings results are received. Next, access report query operation 1214 determines whether the patient would like to access a report on a hospital. If the patient would not like such a report, flow branches NO to query operation 1226, which determines whether the patient would like to research more hospital ratings. If the patient would not like to research more hospital ratings, flow branches NO to terminate operation 1228, which ends process 1200. If the patient would like to research more hospital ratings, flow branches YES to research hospital ratings operation 1204.

If the patient would like to access a report on a hospital, flow branches YES to customize information operation 1218, where the patient may select procedures/medical condition criteria. From customize operation 1218, flow proceeds to free report query operation 1220. If no free report is available, flow branches NO to buy report query 1222. Further, if the patient does not desire to purchase a report, flow from query 1222 branches NO to research more ratings query operation 1226 and then to terminate operation 1228 if the patient does not desire to conduct any further searches for hospital ratings. If buy report query operation 1222 determines that the patient would like to buy a report, flow branches YES to display report operation 1223. From display report operation 1223, link query 1224 determines whether the patient would like to link to a physician report from the hospital report. If such link is desired, flow branches YES to display physician report operation 1225. If no such link is desired, flow branches NO to research query 1226. Research query 1226 determines whether the patient would like to continue researching hospital ratings and reports and branches YES to research operation 1204 if the patient desires to continue such research. On the other hand, if the patient does not desire to continue researching hospitals, flow branches NO to terminate operation 1228, which ends process 1200.

Figure 13:
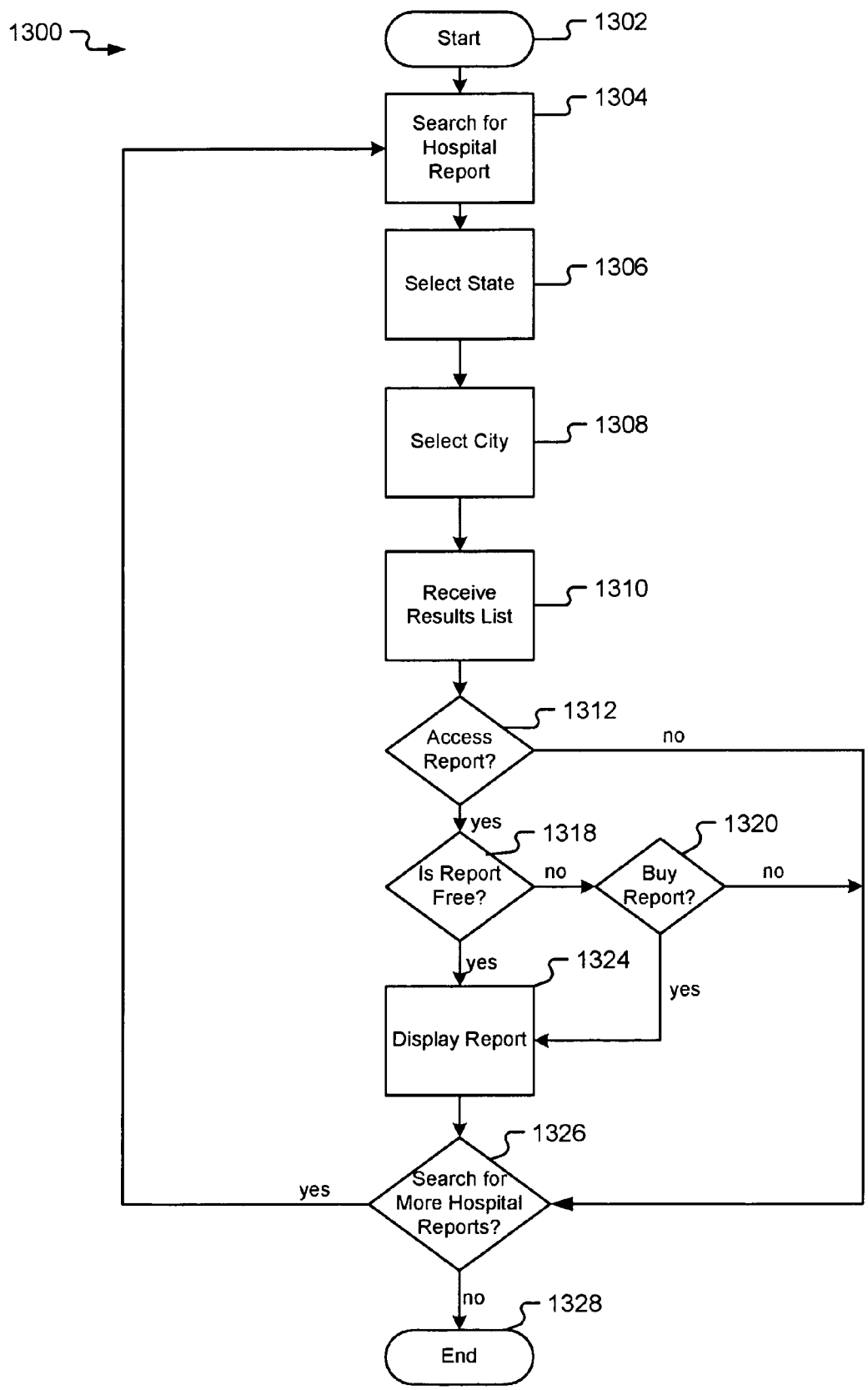
FIG. 13 is a flow diagram illustrating operational characteristics of a search performed for a hospital report using the predetermined Web page providing search capabilities on the company's database shown in FIG. 1, in accordance with an embodiment of the present invention.

Turning now to FIG. 13, process 1300 for searching for a hospital report is shown in accordance with an embodiment of the present invention and begins with start operation 1302 following the patient's access of research Web page 114. From start operation 1302, process 1300 proceeds to search for hospital report operation 1304. Next, the patient selects the state and city desired in operations 1306 and 1308, respectively. Receive operation 1310 receives the results list for the hospitals meeting the specified criteria in select operations 1306 and 1308. From receive operation 1310, process 1300 proceeds to access report query operation 1312. If the patient would not like to access a report, flow branches NO to research more hospital reports query 1326. If additional searches are desired, flow branches YES to search for hospital reports operation 1304. If the patient does not desire to research more hospital reports, flow branches NO to terminate operation 1328. If access report query 1312 determines that the patient would like to access a hospital report, flow branches YES to free report query operation 1318. From free report query operation 1318, the flow and operations 1320-

1328 proceed as illustrated and discussed above in reference to FIGS. 9-12, see, e.g., operations 1220-1228 of FIG. 12.

Figure 14:
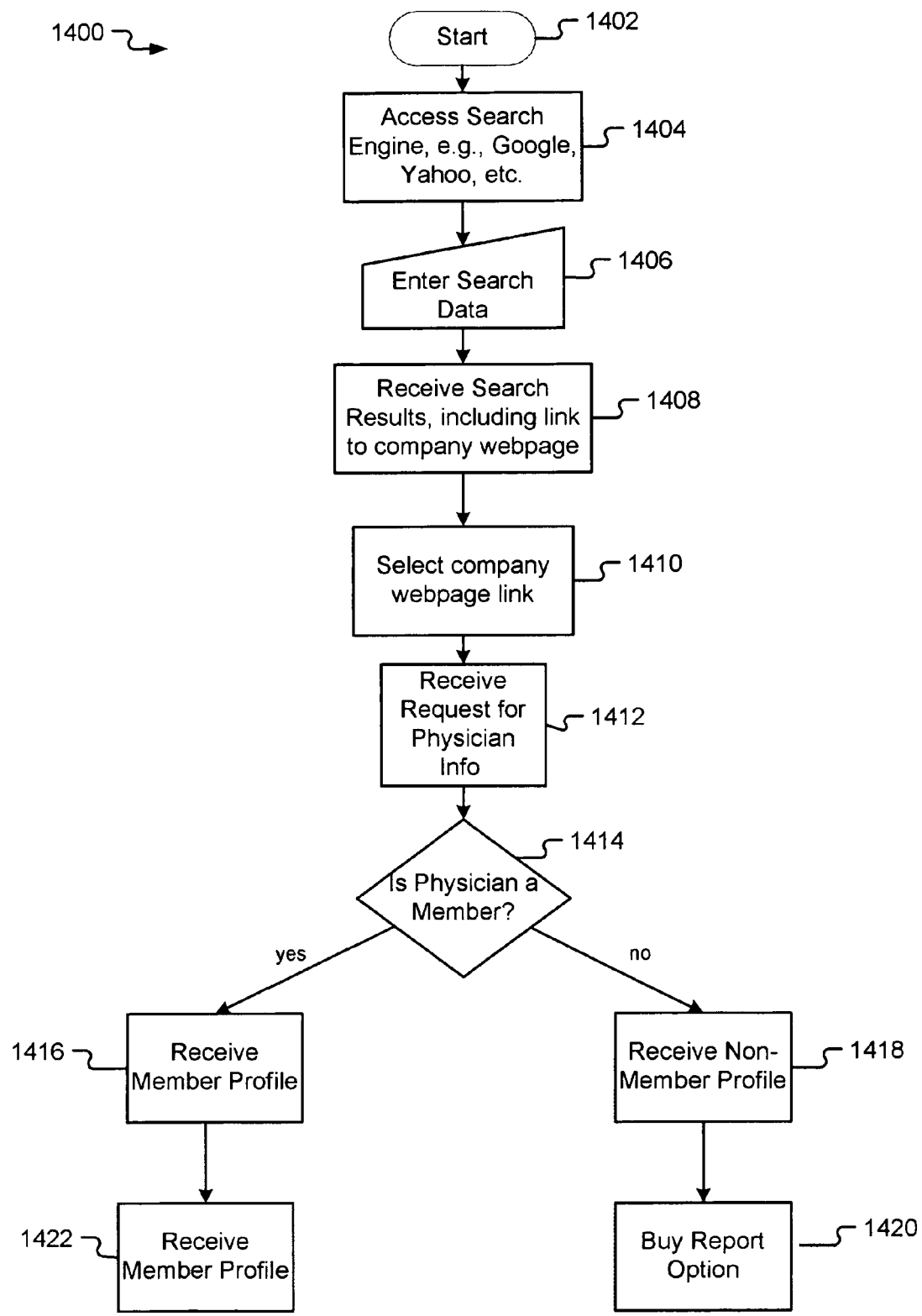
FIG. 14 is a flow diagram illustrating operational characteristics of a search performed for a physician using a search engine external to the company computing system in accordance with an embodiment of the present invention.

Turning now to FIG. 14, process 1400 for performing a search with a search engine for a healthcare provider and receiving a provider profile is shown in accordance with an embodiment of the present invention. Process 1400 relates to a particular embodiment wherein the patient is searching for information on a healthcare provider but may not know where to search, i.e., which Web site has such information. Alternatively, the patient may simply prefer using a search engine as a method of accessing different Web pages. Process 1400 begins with start operation 1402 which is initiated upon the patient's accessing of a search engine, such as, by way of example only, Google, Yahoo, etc. Access operation 1404 relates to a patient's access of one of these search engines from patient terminal 102. Upon accessing the search engine, the patient enters search data, such as the name of the particular physician being searched for, in enter search data operation 1406. Receive search results operation 1408 returns search results, if any, to the patient. Next, the patient selects the company Web page hyperlink in select operation 1410. In receive request for physician information operation 1412, the company computer system, shown in simplified form in FIG. 1 as Web server 110, receives the patient's request for information on a particular healthcare provider.

Query operation 1414 asks whether the physician requested in step 1412 is a member of the company's service. Where the physician is a member, the company system accesses the physician's member profile 112 (FIG. 1) from database 108 and transmits it across local area network 106 and network 104 to patient terminal 102 which receives the member profile in receive operation 1416. Upon reviewing the member profile, the patient may next receive a free report for the member physician in receive operation 1422. Alternatively, if query operation 1414 determines that the physician is not a member, the company system accesses the physician's non-member profile 112 from database 108 and transmits it across local area network 106 and network 104 to patient terminal 102, which receives the non-member profile in receive non-member profile operation 1418. Because the physician is a non-member, the patient is presented with an option to purchase a report on that particular physician in operation 1420.

Figure 15:
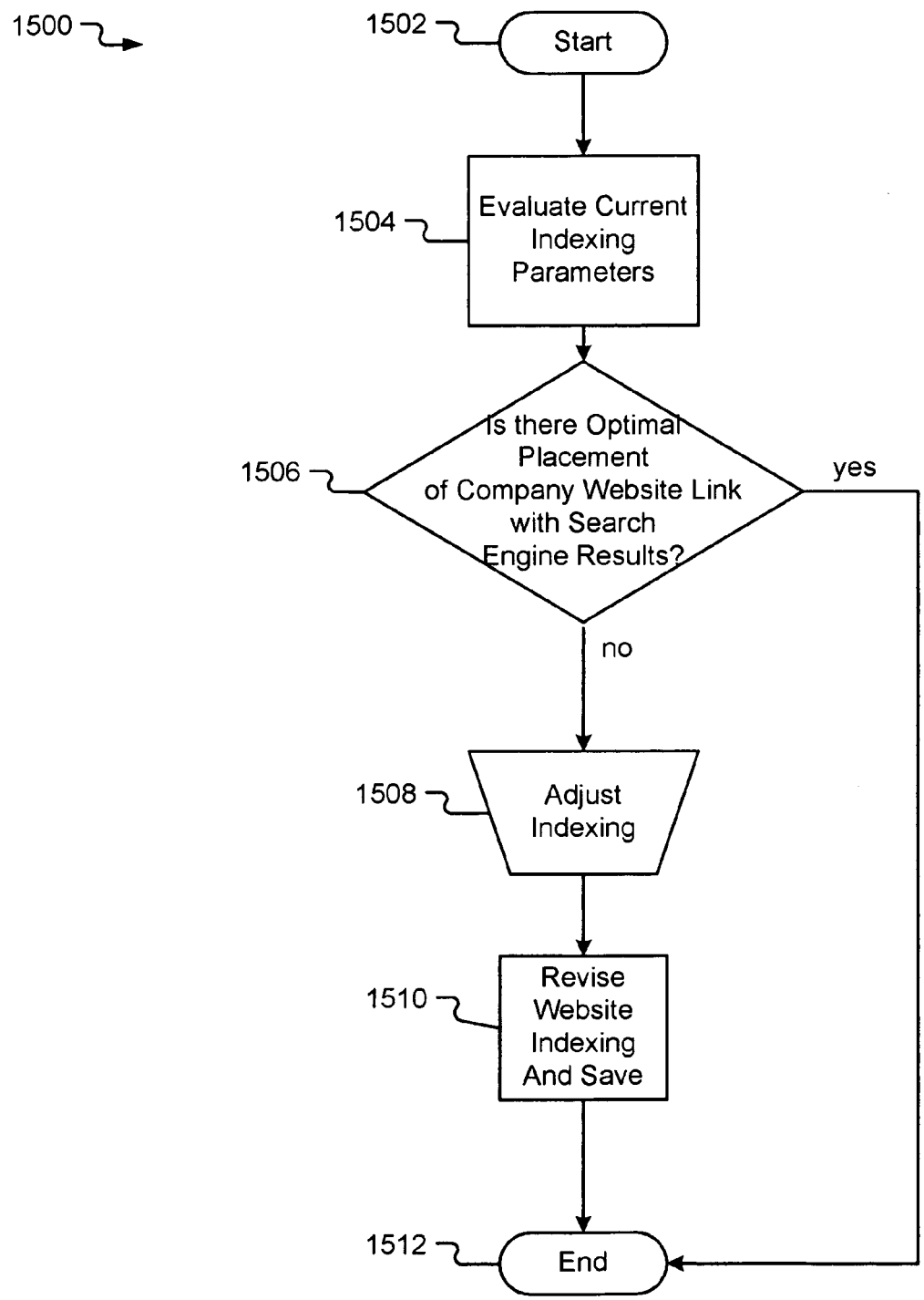
FIG. 15 is a flow diagram illustrating operational characteristics for maintaining indexing parameters for optimal placement of the company Web address and hyperlink in a results page from a search conducted using a search engine external to the company computing system.

While process 1400 provides the operation flow for receiving a healthcare provider profile from a search conducted using a search engine, FIG. 15 describes one embodiment of a process 1500 for obtaining the most favorable index positioning on any search engine, e.g., Google, Yahoo, etc. Start operation 1502 is initiated by a Web developer for the company Web site to analyze the healthcare provider indexing to obtain optimal, i.e., the most favorable, index positioning of the company Web site hyperlink and Web address on the search engine. It is well known in the art that a high index positioning on the search engine results in a high placement of the Web site address and hyperlink on the search engine results page.

Index positioning on the search engine is related directly to the indexability of the Web site at issue. In an embodiment of the present invention, indexability of the company Web site relates to the categorization of healthcare provider names, predetermined breaks in the categories to create predetermined subsets of categories, naming conventions used in listing provider names in Web site indices and categories, and path layout design minimizing the number of "clicks" to reach an indexed entry. Such information is referred to as "indexing parameters," in which indexing parameters relate to the terms used, categorical breaks, or routing paths, i.e., the number of "clicks" used to access the desired information on the company Web site. In an exemplary embodiment, category "A-F" in the index of physician names (140) shown in FIG. 1 is broken into the subset categories of A-Allen, Alleo-Ashe, etc.

In an embodiment, "naming conventions" refer to the information included in listing a provider name in a hyperlinked index. For example, embodiments of the present invention have index parameters involving the terms "M.D." and "Dr." in the Web service's listing of the physician's name in the general index. The inclusion of both "M.D." and "Dr." as two associated indexing parameters creates a greater likelihood that the company Web site will have a favorable indexing position with a search engine and thus be placed at or near the top of the search engine results list. The inclusion of both terms creates more "hits" in the search engine's internal indexing and content counting practice for determining the search results best fitting the search criteria. Similarly, the "breaks" in names, whether of hospitals or of physician last names, etc., is designed to achieve the optimal placement of the company Web page in the search engine results list. The minimization of "clicks" in accessing a path to a desired result is also a type of index parameter related to Web site path layout design which can be used to obtain favorable index positioning on a search engine. Search engines assign favorable index positioning to those entries with fewest "clicks" to obtain the desired information.

High placement in a search engine results list is a valuable marketing technique for the company Web site, and the members thereof, because more patients are likely to hyperlink to those Web sites listed at or near the top of the results list. While particular examples of the indexing parameters, i.e., "breaks," "M.D./Dr.," and "click" minimizations, have been described in accordance with embodiments of this invention, other embodiments involve any type of manipulation of indexing categories to achieve optimal search engine result placement.

From Start operation 1502, process 1500 proceeds to evaluate current indexing parameters in operation 1504 for a particular index entry (e.g., the name of a provider). During evaluate operation 1504, the Web developer determines the current indexing parameters to which the categorizations and indexing on the Web site are set. Evaluate indexing query 1506 determines whether the current indexing parameters are achieving optimal search engine results placement. In an embodiment, such evaluation may involve the testing of sample searches through the use of typical search engines to determine if optimal placement is achieved on the results pages of these search engines. If query operation 1506 determines that optimal placement is being achieved with the current parameters, flow branches YES to end operation 1512. If optimal placement is not being achieved with the current indexing and categorization parameters, flow branches NO to adjust operation 1508. Adjust indexing operation 1508 adjusts, or changes, the current indexing parameter settings to new parameter settings by evaluating the current parameter settings and analyzing the placement positioning with the search engines. From adjust operation 1508, process 1500 proceeds to revise Web site operation 1510 which ensures that the indexing adjustments made in operation 1508 are carried forward throughout the Web site as a whole and are saved appropriately. Terminate operation 1512 ends process 1500.

Figure 16:
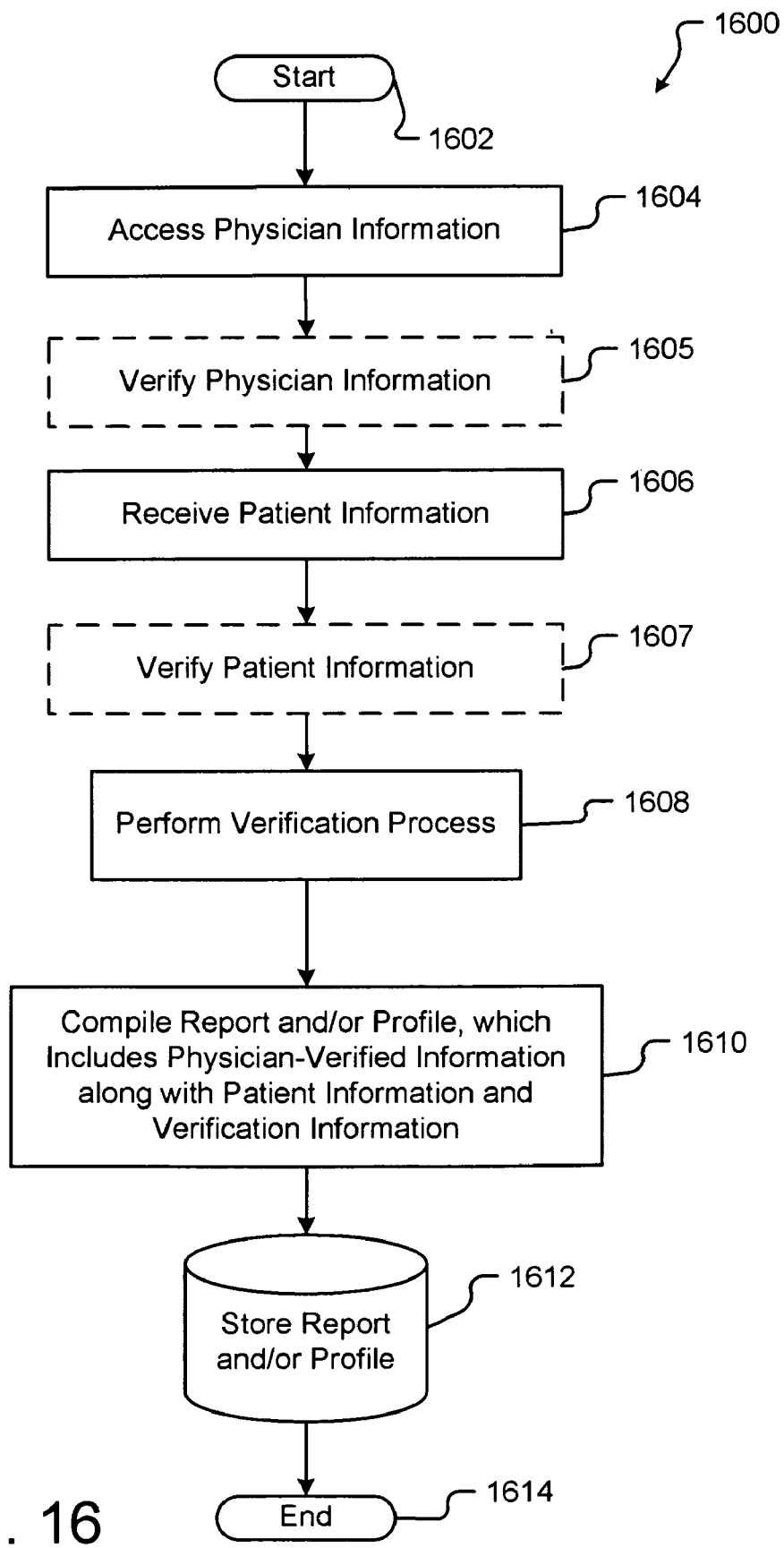
FIG. 16 is a flow diagram illustrating operational characteristics of a process for developing a report or profile of information regarding a particular healthcare provider, including physician-provided information, patient-provided information, and verifications by a third party in accordance with an embodiment of the present invention.

While this disclosure has thus far referred to accessing reports and profiles, a process 1600 for compiling and storing such reports and profiles, including verified information, is shown in FIG. 16 in accordance with an embodiment of the present invention. Start operation 1602 is initiated in response to accessing or obtaining specific physician information. In an embodiment, such information is obtained from the physician himself or herself through a client computer, a network, and a server system such as that depicted in FIG. 1. However, in other embodiments, the information may be obtained through other means. For example, in one embodiment, the information is obtained through an independent third party, such as the company Web service provider, that researches and gathers public information regarding a physician, such as medical license records, board certifications, federal or state disciplinary actions, and other sources of public information, such as advertising by physicians indicating office locations and practice types, insurance company physician listings, etc. Once initiated, the operation flow of the compiling process 1600 passes from Start operation 1602 to access operation 1604, in which information regarding a physician is accessed. The physician information need not be verified at this point, but it may be possible to do so. In an embodiment, the physician information may be verified by an independent third party, by the physician, or by some other individual or entity at optional operation 1605.

From access physician information operation 1604, process 1600 proceeds to receive patient information operation 1606. In an embodiment, receive operation 1606 receives patient-provided information from the patient experience survey 402 illustrated in FIG. 4 and discussed above in reference thereto. In another embodiment, patient ratings and/or comments may be received through other means, such as, by way of example only, a survey sent by regular mail to the company Web service, a ratings and/or comment card completed by the patient at the physician's office or treatment center, etc. Such information may consist of, but is not limited to, ratings and/or recommendations submitted by patients to the system. In an embodiment, the patient-provided information may be verified at optional operation 1607 to certify that the information is from an actual current or former patient of the physician being rated. In an embodiment, such verification may be accomplished by requesting the patient's e-mail address and sending a confirmation to that e-mail address while maintaining a record of the number of times that e-mail address is used in completing a patient survey. In an embodiment, the company Web service provider may limit the number of times within a given timeframe that an individual may complete a patient survey. In another embodiment, such verification may be accomplished by requiring that a patient completing a survey give his or her identity and legal permission to the company Web service provider to verify that he or she is, or was, a patient of the physician being rated. In other embodiments, such verification may be accomplished through any number of means reasonably known to those of ordinary skill in the art.

Operation 1600 next passes to perform verification process operation 1608. Operation 1608 involves the verification of physician-specific information, such as the name of the physician's medical school, graduation date, certification(s), licensure(s), internship(s), residency(ies), fellowship(s), suspension(s), license revocation(s), state or federal censure(s) or reprimand(s), etc. Other information may also be available and verified, such as geographic location. The types of information described herein are intended to be provided as examples only and are in no way intended to delimit the scope of the present invention in any way. While both the access physician information operation 1604 and the receive patient information operation 1606 allow for the potential verification of received and gathered information, such verification is not required at these steps in accordance with embodiments of the present invention. In contrast, perform verification process 1608 is a required step of process 1600 and builds upon the prior steps by further verifying the information provided therein. In an embodiment, verification operation 1608 may be performed by the company, by an independent third party unrelated either to the company or to the healthcare provider, or by any other appropriate entity or individual capable of performing such verification. Verification operation 1608 verifies the accuracy of physician information and patient-provided information received in operations 1604 and 1606, respectively. In some embodiments, verification operation 1608 also verifies the completeness of certain information received in the previous steps, such as, by way of example only, information received and/or gathered regarding a physician's disciplinary action(s), board certification(s), and/or licensure(s), and gathers additional data and information regarding a physician, if such information has not already been received or gathered through other means. In an embodiment, verification operation 1608 verifies the information through the means discussed above. In other embodiments, such verification may be accomplished through any number of means reasonably known to those of ordinary skill in the art.

After verifying the information and data in verification operation 1608, flow proceeds to the compiling, or creation, of healthcare provider profiles and/or reports in compile operation 1610. In an embodiment, compile operation 1610 compiles different sources of information and data into either a report format or profile format. Other embodiments may involve other format types; however, report and profile formats are referred to herein as exemplary embodiments. In an embodiment, the physician-provided information 1604, patient-provided information 1606, and independent third party verification information 1608 is compiled into a report and/or profile 112 (FIG. 1) and stored in database 108. In other embodiments, other types of information and data may be compiled into a report or profile. The particular embodiments described herein are not intended to limit the types of information which may be provided and/or verified. Next, the report or profile 112 created in compile operation 1610 is stored in database 108 in store operation 1612. Terminate operation 1614 ends process 1600.

Figure 17:
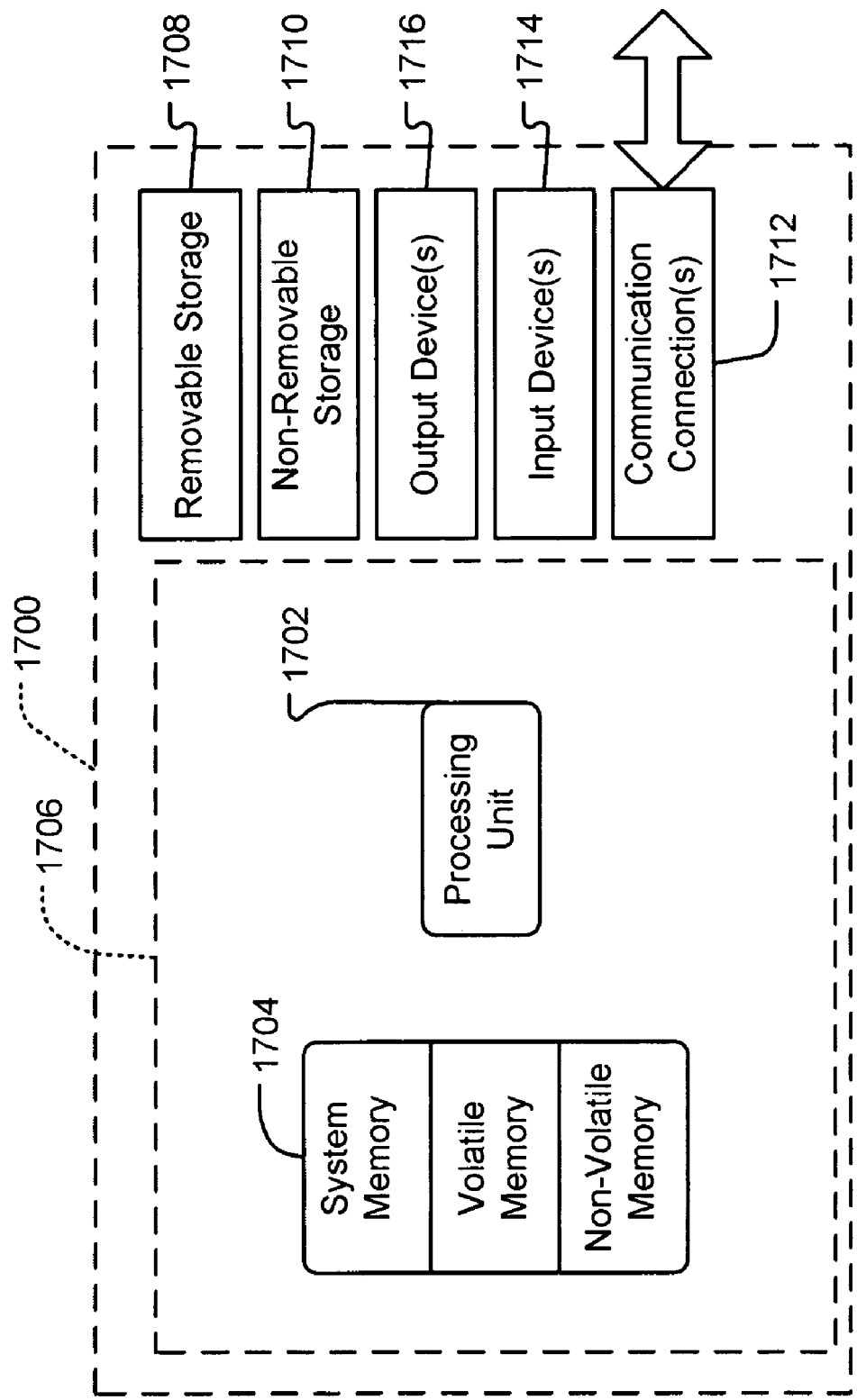
FIG. 17 depicts an exemplary computing system upon which embodiments of the present invention may be implemented.

Turning now to the exemplary computing system itself, FIG. 17 illustrates a computer system 1700 with the storage and information dissemination capabilities shown with respect to the healthcare provider information network in FIG. 1 in accordance with embodiments of the present invention. The system 1700 has at least one processor 1702 and memory 1704.

In its most basic configuration, computing system 1700 is illustrated in FIG. 17 by dashed line 1706. Additionally, system 1700 may also include additional storage for storing the reports and/or profiles 112 (FIG. 1) of the present invention. Such additional storage (removable and/or non-removable) includes, but is not limited to, magnetic or optical disks or tape. This additional storage is illustrated in FIG. 17 by removable storage 1708 and non-removable storage 1710. Computer storage media includes volatile and nonvolatile, removable and non-removable media implemented in any method or technology for storage of information such as computer readable instructions, data structures, program modules or other data. Memory 1704, removable storage 1708 and non-removable storage 1710 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by system 1700. Any such computer storage media may be part of system 1700. Depending on the configuration and type of computing device, memory 1704 may be volatile, non-volatile or some combination of the two.

System 1700 may also contain communications connection(s) 1712 that allow the device to communicate with other devices. Additionally, system 1700 may have input device(s) 1714 such as keyboard, mouse, pen, voice input device, touch input device, etc. for entering data and information, such as search criteria entered by the patient at patient terminal 102 (FIG. 1). Output device(s) 1716 such as a display, speakers, printer, etc. may also be included. All these devices are well known in the art and need not be discussed at length here.

Computer system 1700 typically includes at least some form of computer readable media. Computer readable media can be any available media that can be accessed by system 1700. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by system 1700. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

With the computing environment of FIG. 17 in mind, logical operations of the various exemplary embodiments described herein may be implemented: (1) as a sequence of computer implemented acts or program modules running on a computing system; and/or (2) as interconnected machine logic circuits or circuit modules within the computing system.

Having described the embodiments of the present invention with reference to the figures above, it should be appreciated that numerous modifications may be made to the present invention that will readily suggest themselves to those skilled in the art and which are encompassed in the spirit of the invention disclosed and as defined in the appended claims. Indeed, while presently preferred embodiments have been described for purposes of this disclosure, various changes and modifications may be made which are well within the scope of the present invention. For example, the present invention may not be limited specifically to healthcare provider information but, instead, may be applicable to any kind of professionals, such as engineers, accountants, veterinarians, dentists, etc. Additionally, the order of operations shown in the flow diagrams illustrated in the figures herein is provided for illustrative purposes only and, in accordance with other embodiments, may be modified or performed simultaneously.

Furthermore, it should be appreciated that the scope of the present invention accommodates other operations that may be added or removed depending on the needs of the particular entity or entities implementing or using the system.

Similarly, although this disclosure has used language specific to structural features, methodological acts, and computer-readable media containing such acts, it is to be understood that the present invention defined in the appended claims is not necessarily limited to the specific structure, acts, or media described herein. The specific structure, acts, or media are disclosed as exemplary embodiments of implementing the claimed invention. The invention is defined by the appended claims.

What is claimed is:

1. A computer-implemented method of providing healthcare provider information to potential patients, said method comprising:
   receiving, by a Web server computer of a company providing a service for connecting healthcare providers with the potential patients, a request for information regarding a first healthcare provider, wherein the Web server computer comprises at least one computer processor and memory;
   accessing healthcare provider-verified information about the first healthcare provider, wherein the healthcare provider-verified information is received from the first healthcare provider and comprises three or more from the group consisting of: specialty information, medical philosophy, gender, age, years in profession, years in practice, awards, honors, professional appointments, professional memberships, publications, languages, and hobbies;
   compiling, by the at least one computer processor, patient-provided information regarding the first healthcare provider, wherein the patient-provided information comprises patient ratings from one or more past or current patients of the first healthcare provider, and wherein the patient ratings are received from an on-line patient experience survey completed on a company Web site by the one or more past or current patients of the first healthcare provider, and wherein the company Web site is managed by the company providing the service for connecting healthcare providers with the potential patients;
   compiling information regarding the first healthcare provider verified by an independent third-party source, wherein the information verified by the independent third-party source comprises three or more from the group consisting of: board certification, licensure, disciplinary action information, medical school, medical internship, medical residency, and medical fellowship information;
   creating, by the at least one computer processor, a healthcare provider report on the first healthcare provider using the healthcare provider-verified information, the patient-provided information, and the information verified by the independent third-party source, wherein the healthcare provider report on the first healthcare provider includes comparison ratings of healthcare providers; and
   providing access to the healthcare provider report on the first healthcare provider over a computer network.

2. The method as defined in claim 1, wherein the patient-provided information is obtained through data collected through the method comprising:
- the one or more past or current patients of the first healthcare provider accessing a report on the first healthcare provider over the computer network;
- the one or more past or current patients selecting to complete the on-line patient experience survey;
- the one or more past or current patients completing the experience survey and providing an e-mail address; and
- transmitting the completed experience survey to the Web server of the company providing the service for connecting healthcare providers with the potential patients.

3. The method as defined in claim 2, further comprising a method for verifying and compiling the data, the method comprising:
- determining whether a first past or current patient has completed a maximum number of surveys for a predetermined time period;
- if the first past or current patient has not reached the maximum number of surveys, transmitting a confirmation e-mail to the e-mail address provided;
- determining if the confirmation e-mail was successfully transmitted; and
- if the e-mail was successfully transmitted, compiling the data provided by the first past or current patient with other relevant data in a company database comprised of healthcare provider information.

4. The method as defined in claim 1, wherein the healthcare provider report includes a hyperlink to an affiliated hospital, medical center, or other type of treatment center.

5. The method as defined in claim 1, wherein the access to the healthcare provider report is obtained through a predetermined Web page that provides search capabilities for a database comprised of healthcare provider information.

6. The method as defined in claim 5, wherein the search capabilities permit a search based on one or more from the group consisting of: name, medical specialty, gender, state, city, procedure, diagnosis, procedure, and location criteria.

7. The method as defined in claim 6, wherein the search of the database produces a results list of one or more healthcare providers satisfying the search criteria, wherein the results list includes the first healthcare provider.

8. The method as defined in claim 7, wherein the results list further includes an advertisement for the first healthcare provider with a hyperlink to information on the first healthcare provider.

9. The method as defined in claim 7, further comprising:
- determining from the results list whether a particular healthcare provider is a member of the company managing the Web site; and
- if the particular healthcare provider is a member of the company managing the Web site, providing enhanced services for the member healthcare provider on the Web site.

10. The method as defined in claim 9, wherein the enhanced services comprise making report information on the member healthcare provider available at no charge to the potential patients.

11. The method as defined in claim 9, wherein the enhanced services comprise favorable positioning in the results list.

12. The method as defined in claim 1, further comprising:
- maintaining a record of whether the healthcare provider report on the first healthcare provider should be made available to a first potential patient at no charge; and
- requiring payment of a fee to access the healthcare provider report on the first healthcare provider if the report is not recorded as being available at no charge.

13. The method as defined in claim 12, wherein the required fee is adjusted to account for applicable discounts.

14. The method as defined in claim 1, wherein the first healthcare provider is a physician.

15. An on-line information system for connecting healthcare providers with potential patients, the system comprising:
- at least one computer processor; and
- memory coupled with and readable by the at least one computer processor and comprising a series of instructions that, when executed by the at least one computer processor, cause the at least one computer processor to:
  - receive a request for information regarding a first healthcare provider;
  - access healthcare provider-verified information about the first healthcare provider, wherein the healthcare provider-verified information is received from the first healthcare provider and comprises three or more from the group consisting of: specialty information, medical philosophy, gender, age, years in profession, years in practice, awards, honors, professional appointments, professional memberships, publications, languages, and hobbies;
  - compile patient-provided information regarding the first healthcare provider, wherein the patient-provided information comprises patient ratings from one or more past or current patients of the first healthcare provider, and wherein the patient ratings are received from an on-line patient experience survey completed on a company Web site by the one or more past or current patients of the first healthcare provider, and wherein the company Web site is managed by a company providing a service for connecting healthcare providers with the potential patients;
  - compile healthcare provider information regarding the first healthcare provider verified by an independent third-party source, wherein the information verified by the independent third-party source comprises three or more from the group consisting of: board certification, licensure, disciplinary action information, medical school, medical internship, medical residency, and medical fellowship information;
  - create a healthcare provider report on the first healthcare provider using the healthcare provider-verified information, the patient-provided information, and the information verified by the independent third-party source, wherein the healthcare provider report on the first healthcare provider includes comparison ratings of healthcare providers; and
  - provide access to the healthcare provider report on the first healthcare provider over a computer network.

16. The on-line information system defined in claim 15, wherein:
- the healthcare provider report is obtained through one or more from the group consisting of: a predetermined Web page that provides search capabilities on its database and a third-party search engine; and
- the search capabilities of the predetermined Web page permit searching based on one or more from the group consisting of: name, medical specialty, gender, state, city, procedure, diagnosis, and location criteria.

17. The on-line information system defined in claim 16, wherein the at least one computer processor:
  produces a results list of one or more healthcare providers satisfying received search criteria, wherein the results list includes the first healthcare provider;
  determines from the results list whether the first healthcare provider is a member of the company managing the Web site; and
  if the first healthcare provider is a member of the company managing the Web site, provides enhanced services for the member healthcare provider on the Web site, wherein the enhanced services comprise making report information on the member healthcare provider available at no charge to the potential patients.

* * * * *